US011585760B2

(12) United States Patent
Hagen et al.

(10) Patent No.: US 11,585,760 B2
(45) Date of Patent: Feb. 21, 2023

(54) OPTICAL SIGNAL DETECTION MODULES AND METHODS

(71) Applicant: Gen-Probe Incorporated, San Diego, CA (US)

(72) Inventors: Norbert Hagen, San Diego, CA (US); George Walker, II, San Diego, CA (US); David Combs, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 394 days.

(21) Appl. No.: 16/633,985

(22) PCT Filed: Jul. 25, 2018

(86) PCT No.: PCT/US2018/043594
§ 371 (c)(1),
(2) Date: Jan. 24, 2020

(87) PCT Pub. No.: WO2019/023294
PCT Pub. Date: Jan. 31, 2019

(65) Prior Publication Data
US 2020/0217794 A1      Jul. 9, 2020

Related U.S. Application Data

(60) Provisional application No. 62/537,145, filed on Jul. 26, 2017.

(51) Int. Cl.
*G01N 21/64* (2006.01)
*C12Q 1/6806* (2018.01)
*G02B 6/08* (2006.01)

(52) U.S. Cl.
CPC ....... *G01N 21/6486* (2013.01); *C12Q 1/6806* (2013.01); *G01N 21/6452* (2013.01); *G02B 6/08* (2013.01); *G01N 2021/6484* (2013.01)

(58) Field of Classification Search
CPC .......... G01N 21/6452; G01N 21/6486; G01N 2021/6484; C12Q 1/6806; G02B 6/08
See application file for complete search history.

(56) References Cited

U.S. PATENT DOCUMENTS 5,998,802 A   12/1999 Struye et al.
6,392,241 B1   5/2002 Rushbrooke et al.
(Continued)

FOREIGN PATENT DOCUMENTS

EP   1962084 A1   8/2008
EP   2463643 A1   6/2012
(Continued)

OTHER PUBLICATIONS

PCT International Search Report and Written Opinion, International Patent Application No. PCT/US2018/043594, dated Oct. 4, 2018.
(Continued)

*Primary Examiner* — Kevin K Pyo
(74) *Attorney, Agent, or Firm* — Charles B. Cappellari; Sterne, Kessler, Goldstein & Fox P.L.L.C.

(57) ABSTRACT

An apparatus for detecting an optical signal emissions includes signal transmission fibers. Each fiber includes cores having the same spatial core arrangement at each end. The first ends are configured to be optically coupled to the signal emission sources. Each fiber is configured to transmit an optical signal between the first end and the second. The apparatus can also include a frame assembly securing the first ends of the fibers in a first spatial fiber arrangement corresponding to a spatial arrangement of the signal emission sources. The frame assembly can also secure the second ends of the fibers in a second spatial fiber arrangement different from the first spatial fiber arrangement. The apparatus can also include at least one signal detector configured to be optically coupled to the second ends of the fibers, and
(Continued)

configured to detect an optical signal emitted by each signal emission source.

25 Claims, 20 Drawing Sheets

(56) References Cited

U.S. PATENT DOCUMENTS

| | | |
|---|---|---|
| 2003/0001122 A1 | 1/2003 | Shimizu et al. |
| 2008/0056950 A1 | 3/2008 | Weisbuch et al. |
| 2014/0263984 A1 | 9/2014 | Hagen et al. |
| 2016/0060680 A1 | 3/2016 | Buse et al. |
| 2021/0157060 A1* | 5/2021 | Hagen .................. G01N 21/253 |

FOREIGN PATENT DOCUMENTS

| | | |
|---|---|---|
| EP | 2685299 A1 | 1/2014 |
| WO | 2011061735 A2 | 5/2011 |
| WO | WO 2011/061735 A2 | 5/2011 |

OTHER PUBLICATIONS

EPO Communication pursuant to Article 94(3) EPC, European Application No. 18752943.3, dated Apr. 7, 2022.

* cited by examiner

| Interface Position | Reformatter Position |
|---|---|
| T1 | F21 |
| T2 | F20 |
| T3 | F19 |
| T4 | F18 |
| T5 | F17 |
| T6 | F26 |
| T7 | F25 |
| T8 | F16 |
| T9 | F14 |
| T10 | F13 |
| T11 | F27 |
| T12 | F24 |
| T13 | F23 |
| T14 | F12 |
| T15 | F11 |
| T16 | F28 |
| T17 | F32 |
| T18 | F6 |
| T19 | F9 |
| T20 | F10 |
| T21 | F30 |
| T22 | F31 |
| T23 | F4 |
| T24 | F5 |
| T25 | F7 |
| T26 | F33 |
| T27 | F34 |
| T28 | F35 |
| T29 | F2 |
| T30 | F3 |

FIG. 11

OPTICAL SIGNAL DETECTION MODULES AND METHODS

BACKGROUND

Field

This disclosure relates to apparatuses and methods for detecting optical signals emitted by signal emission sources.

Background

A sample assay instrument can perform assays on samples to determine the presence or amounts of particular analytes in the samples. The analytes can include for example, biological antigens, cell or genetic abnormalities, or disease-associated pathogens in an organism or biological sample. These assays can use probes to identify the desired analytes. Probes may include, for example, labels such as radiolabels, fluorophores or fluorescent dyes, biotins, enzymes, or chemiluminescent compounds that emit a detectable signal.

To detect different analytes, different probes that emit detectibly different signals can be used. For example, different probes configured to detect different analytes can be formulated with fluorophores that fluoresce at a respective predetermined wavelength when exposed to a respective excitation wavelength. Assays for detecting different analytes can be performed in parallel by alternately exposing the sample to different excitation wavelengths and detecting the level of fluorescence at the wavelength of interest that corresponds to the probe for each analyte. Parallel processing can be performed using different signal detecting modules configured to generate excitation signals of different wavelengths, and to measure emission signals of different wavelengths. The strength of the emitted optical signal can be proportional to the amount of the analyte present in the sample. Accordingly, by periodically measuring, a signal indicative of the presence and growth of the analyte can be detected.

BRIEF SUMMARY

In some embodiments, an apparatus for detecting an optical signal emission from a plurality of potential signal emission sources includes a plurality of signal transmission fibers. Each fiber can include a plurality of cores having a first spatial core arrangement at a first end, and a second spatial core arrangement at a second end that is the same as the first spatial arrangement. The first ends are configured to be optically coupled to the plurality of potential signal emission sources. Each fiber is configured to transmit an optical signal between the first end and the second. The apparatus can also include a frame assembly securing the first ends of the plurality of signal transmission fibers in a first spatial fiber arrangement corresponding to a spatial arrangement of the signal emission sources. The frame assembly can also secure the second ends of the plurality of signal transmission fibers in a second spatial fiber arrangement different from the first spatial fiber arrangement. The apparatus can also include at least one signal detector configured to be optically coupled to the second end of each signal transmission fiber, and configured to detect an optical signal emitted by each signal emission source.

In some embodiments, the at least one signal detector comprises a plurality of signal detectors, and each signal detector is configured to generate an excitation signal of a different predetermined excitation wavelength and to detect an emission signal of a different predetermined emission wavelength. The apparatus can include a signal detector carrier, and the plurality of signal detectors can be mounted to the signal detector carrier. The signal detector carrier is configured to move such that each signal detector is sequentially optically coupled to the second ends of the signal transmission fibers.

The first spatial fiber arrangement is rectangular and includes two or more rows. Each row can include two or more of the first ends of the signal transmission fibers.

The second spatial fiber arrangement can include one of (a) one or more circles each comprising a plurality of second ends of the plurality of signal transmission fibers, and (b) one or more bundles of a plurality of second ends of the plurality of signal transmission fibers. The signal detector carrier can include a rotatable carousel configured to move the one or more signal detectors along a path corresponding to the one or more circles of the second spatial fiber arrangement.

The frame assembly can include an interface plate securing the first ends of the signal transmission fibers in the first spatial fiber arrangement, and a base, spaced apart from the interface plate, securing the second ends of the signal transmission fibers in the second spatial fiber arrangement. The frame assembly can also include heat dissipating fins extending from the interface plate.

The apparatus can also include a plurality of signal coupling elements, each being operatively disposed with respect to the respective first end of each signal transmission fiber.

A minimum bend radius of the plurality of signal transmission fibers is equal to or less than about 10 mm. For example, the minimum bend radius of the plurality of signal transmission fibers is equal to or less than about 5 mm.

In some embodiments, a method of diagnosing an optical misalignment between a signal detector and a first end of signal transmission fiber includes emitting an optical signal from the signal detector. The method further includes transmitting the emitted optical signal from the first end of the signal transmission fiber to a second end the signal transmission fiber, and determining whether an intensity pattern of the transmitted optical signal at the second end is symmetric or asymmetric. A symmetric intensity pattern indicates that the signal detector and the first end of signal transmission fiber are optically aligned, and an asymmetric intensity pattern indicates that the signal detector and the first end of the signal transmission fiber are optically misaligned.

In some embodiments, the determining step is manual. For example, the determining step can include visually inspecting the second end of the signal transmission fiber. The visually inspecting step can include using a magnifier that generates a magnified image of the second end of the signal transmission fiber. The magnifier can include a magnifying glass, or a camera system having a camera that acquires an image of the second end of the signal transmission fiber, and a display that displays a magnified image based on the acquired image of the second end of the signal transmission fiber.

In some embodiments, the determining step is automatic. For example, the determining step can include generating an image of the second end of the signal transmission fiber, and automatically analyzing the generated image to determine whether the intensity pattern of the transmitted optical signal at the second end is symmetric or asymmetric.

In some embodiments, the method also includes, when the intensity pattern of the transmitted optical signal at the second end is asymmetric, adjusting the relative position between the signal detector and the first end of the signal transmission fiber. The magnitude and direction of the relative position adjustment between the signal detector and the first end of the signal transmission fiber can be determined based on the intensity pattern of the transmitted optical signal.

The emitting, transmitting, and determining steps can occur during the manufacturing of a sample assay instrument comprising the signal detector and the signal transmission fiber. Or the emitting, transmitting, and determining steps can occur during routine maintenance of a sample assay instrument comprising the signal detector and the signal transmission fiber, or while trouble shooting a problem with the sample assay instrument after being manufactured.

Further features and advantages of the embodiments, as well as the structure and operational of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE FIGURES

The accompanying drawings, which are incorporated herein and form part of the specification, illustrate the present disclosure and, together with the description, further serve to explain the principles of the disclosure.

FIG. 11 is a table showing the mapping between the fiber positions at the interface plate and the fiber positions at the base of a frame assembly, according to an embodiment.

The features and advantages of the embodiments will become more apparent from the detailed description set forth below when taken in conjunction with the drawings, in which similar reference characters identify corresponding elements throughout.

DETAILED DESCRIPTION

Figure 1:
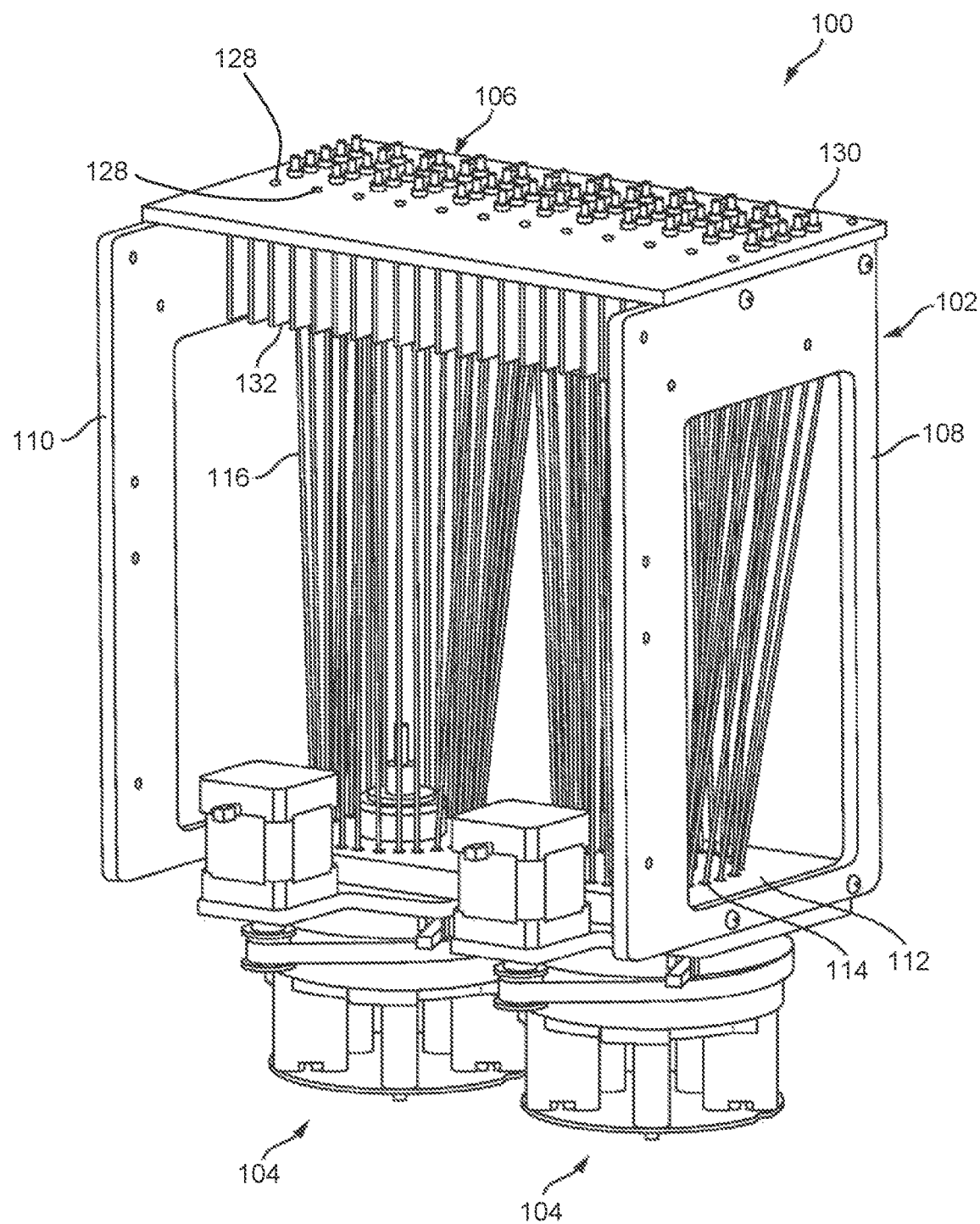
FIG. 1 is a perspective view of a signal detection module, according to an embodiment.

Reference will now be made in detail to examples of the present disclosure, which are illustrated in the accompanying drawings. Wherever possible, the same or similar reference numbers will be used throughout the drawings to refer to the same or like parts. Although embodiments of the current disclosure are described with reference to its application in an instrument that performs molecular genetics related sample analysis, this is only exemplary. As a person skilled in the art would recognize, embodiments of the current disclosure may be applied to any application.

Unless defined otherwise, all terms of art, notations and other scientific terms/terminology used herein have the same meaning as is commonly understood by one of ordinary skill in the art to which this disclosure belongs. All patents, applications, published applications and other publications (literature) referred to herein are incorporated by reference in their entirety. If a definition set forth in this section is contrary to or otherwise inconsistent with a definition set forth in the literature incorporated herein by reference, the definition set forth in this section prevails over the definition that is incorporated by reference.

References in the specification to "one embodiment," "an embodiment," a "further embodiment," "an example embodiment," "some aspects," "a further aspect," "aspects," "for example," "exemplary," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic is also a description in connection with other embodiments whether or not explicitly described. Further, as used herein, "a" or "an" means "at least one" or "one or more."

Further, the description below may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

As used herein, a "sample assay instrument" refers to any instrument capable of performing an assay on a sample and rendering a result. For example, a sample assay instrument includes any diagnostic instrument capable performing an assay on a sample to determine the presence of an analyte in the sample. Any diagnostic instrument capable of performing a hybridization assay, a molecular assay including a nucleic-acid-based amplification reaction, a sequencing assay, an immunoassay, or chemistry assay on a sample is included in this definition of a sample assay instrument. Exemplary diagnostic instruments capable performing an assay on a sample to determine the presence of an analyte in the sample include the Tigris®, Panther®, and Panther Fusion® systems sold by Hologic, Inc., Marlborough, Mass., as well as any of the diagnostic instruments disclosed in U.S. Patent Application Publication No. 2016/0060680, published Mar. 3, 2016.

As used herein, a "sample" refers to any material to be analyzed, regardless of the source. The material can be in its native form or any stage of processing (e.g., the material can be chemically altered or it can be one or more components of a sample that have been separated and/or purified from one or more other components of the sample). A sample can be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

Exemplary Sample Assay Instruments

In some embodiments, a sample assay instrument is configured to transmit and/or measure signals emitted by potential emission signal sources for use during a nucleic acid diagnostic assays, for example, "real-time" amplification assays and "end-point" amplification assays. Exemplary nucleic acid diagnostic assay can include performing polymerase chain reactions (PCR), transcription-mediated amplification reactions (TMA), ligase chain reactions (LCR), strand displacement amplification reactions (SDA), and loop-mediated isothermal amplification reactions.

In some embodiments, the sample assay instrument is configured to perform real-time implication assays. Real-time amplification assays can be used to determine the presence and amount of a target nucleic acid in a sample. The target nucleic acid can be, for example, derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations.

In some embodiments, the sample assay instrument is configured to perform end-point amplification assays. In end-point amplification assays, the presence of amplification products containing the target sequence or its complement is determined at the conclusion of an amplification procedure. In contrast, the amount of amplification products containing the target sequence or its complement is determined during a "real-time" amplification assays. In exemplary real-time amplification assays, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

In some exemplary real-time amplification assays, the probes can be unimolecular, self-hybridizing probes having a pair of interacting labels that interact and thereby emit different signals, depending on whether the probes are in a self-hybridized state or hybridized to the target sequence or its complement. Other probes, for example, complementary, bimolecular probes and probes labeled with an intercalating dye, can be used in some real-time amplification embodiments. Exemplary interacting labels include enzyme/substrate, enzyme/cofactor, luminescent/quencher, luminescent/adduct, dye dimers, and Forrester energy transfer pairs.

The embodiments of the present disclosure operate regardless of the particular labeling scheme utilized provided the moiety to be detected can be excited by a particular wavelength of light and emits a distinguishable emission spectra.

In some exemplary real-time amplification assays, interacting labels can include a fluorescent moiety, or other emission moiety, and a quencher moiety, such as, for example, 4-(4-dimethylaminophenylazo)benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to a nucleic acid present in the sample, the fluorescent and quencher moieties are separated from each other, and light energy emitted by the fluorescent moiety can be detected. Fluorescent moieties having different and distinguishable excitation and emission wavelengths are often combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties. In another embodiment, different fluorescent moieties having the same excitation wavelength, but different and distinguishable emission wavelengths are combined with different probes. The presence and amount of target nucleic acids associated with each probe can be determined by exposing the sample to a specific wavelength light energy and the light emission from the sample at the different wavelengths corresponding to the different fluorescent moieties is measured.

In one example of a multiplex, real-time amplification assay, the following may be added to a sample prior to initiating the amplification reaction: (1) a first probe having a quencher moiety and a first fluorescent dye (having an excitation wavelength $\lambda_{ex1}$ and emission wavelength $\lambda_{em1}$) joined to its 5' and 3' ends and having specificity for a nucleic acid sequence derived from HCV; a second probe having a quencher moiety and a second fluorescent dye (having an excitation wavelength $\lambda_{ex2}$ and emission wavelength $\lambda_{em2}$) joined to its 5' and 3' ends and having specificity for a nucleic acid sequence derived from HIV Type 1 (HIV-1); and a third probe having a quencher moiety and a third fluorescent dye (having an excitation wavelength $\lambda_{ex3}$ and emission wavelength $\lambda_{em3}$) joined to its 5' and 3' ends and having specificity for a nucleic acid sequence derived from West Nile virus (WNV). After combining the probes in a sample with amplification reagents, the samples can be periodically and alternately exposed to excitation light at wavelengths $\lambda_{ex1}$, $\lambda_{ex2}$, and $\lambda_{ex3}$, and then measured for emission light at wavelengths $\lambda_{em1}$, $\lambda_{em2}$, and $\lambda_{em3}$, to detect the presence (or absence) and amount of all three viruses in the single sample. The components of an amplification reagent will depend on the assay to be performed, but can contain at least one amplification oligonucleotide, such as a primer, a promoter-primer, and/or a promoter oligonucleotide, nucleoside triphosphates, and cofactors, such as magnesium ions, in a suitable buffer, according to some embodiments.

In some multiplex embodiments, suitable dyes include rhodamine dyes (e.g., tetramethyl-6-rhodamine ("TAMRA") and tetrapropano-6-carboxyrhodamine ("ROX")) and fluorescein dyes (e.g., 6-carboxyfluorescein ("FAM")) each in combination with a DABCYL quencher. In some embodiments, other suitable dyes include 5'-hexachlorofluorescein phosphoramidite ("HEX"), and 2', 7'-dimethoxy-4', 5'-dichloro-6-carboxyfluorescein ("JOE"), DyLight 647, and DyLight 677. Because the dyes are excited at different wavelengths, each signal detector can be tailored to emit an excitation light at or near the desired excitation wavelength (i.e., color) for the particular dye that the fluorometer is intended to detect. Accordingly, component selection for the detector/fluorometer will, in many instances, be governed by the particular dye for which signal detector is intended. For example, the particular light source (e.g., the particular LED) used will depend on the dye for which the fluorometer is intended to detect.

Where an amplification procedure is used to increase the amount of a target sequence, or its complement, present in a sample before detection occurs, a "control" can be included to ensure that amplification has taken place. Such a control can be a known nucleic acid sequence that is unrelated to the sequence(s) of interest. A probe (i.e., a control probe) having specificity for the control sequence and having a unique fluorescent dye (i.e., the control dye) and quencher combination can be added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus calling into question the results from that assay. Alternatively, failure to detect emission light may be due to failure or deteriorated mechanical and/or electrical performance of an instrument (described below) for detecting the emission light.

Apparatus and procedures embodying aspects of the disclosure may be used a variety of nucleic acid amplification procedures, including in conjunction with real-time PCR, which requires accurate/rapid thermocycling between denaturation (e.g., about 95° C.), annealing (e.g., about 55° C.), and synthesis (e.g., about 72° C.) temperatures. For this purpose, receptacles containing a reaction mixture for PCR are held in a thermocycler configured to effect temperature cycling between the denaturation, annealing, and synthesis phases. Emission signal monitoring (e.g., of fluorescence) of the contents of the receptacles held in the thermocycler occurs at one or many color wavelengths during each temperature cycle between 95° C., 55° C., and synthesis 72° C.

One round of PCR synthesis will result in new strands of indeterminate length which, like the parental strands, can hybridize to the amplification oligonucleotides upon denaturation and annealing. These products accumulate arithmetically with each subsequence cycle of denaturation, annealing to amplification oligonucleotides, and synthesis. The second cycle of denaturation, annealing, and synthesis produces two single-stranded products that together compose a discrete double-stranded product which comprises the length between the amplification oligonucleotide ends. Each strand of this discrete product is complementary to one of the two amplification oligonucleotides and can therefore participate as a template in subsequent cycles. The amount of this product doubles with every subsequent cycle of synthesis, denaturation and annealing. This accumulates exponentially so that 30 cycles should result in a $2^{28}$-fold (270 million-fold) amplification of the discrete product.

Exemplary Signal Detection Modules

Detection and, optionally, measurement of optical emission signals from optical emission signal sources, such as receptacles containing samples undergoing amplification as described above can be performed with a signal detection module, in some embodiments. A signal detection module according to an embodiments is indicated by reference number 100 in FIG. 1. Signal detection module 100 can be part of a sample assay instrument as described above.

Signal detection module 100 can include an frame assembly 102. Signal detection module 100 can also include one or more, for example, two as shown in FIG. 1, signal detector heads 104 that are attached to a lower end of frame assembly 102. Frame assembly 102 can also include an interface plate 106 that is attached to an upper end of frame assembly 102. In some embodiments, frame assembly 102 includes two opposing sides 108, 110. Sides 108, 110 can be generally vertical as shown in FIG. 1. Frame assembly 102 can also include a base 112 attached to the bottom ends of sides 108, 110. Base 112 can define a plurality of fiber-positioning holes 114. Note that the designations that sides 108, 110 are vertical is merely to provide a convenient reference with respect to the orientation of signal detection module 100 as shown in FIG. 1, and such term of orientation is not intended to be limiting. Accordingly, signal detection module 100 could be oriented at any angle, including vertical or horizontal, or any angle therebetween.

Frame assembly 102 can have a variety of purposes, including organizing and arranging a plurality of optical transmission fibers 116 that extend between an excitation/ emission area and a detection area. In some embodiments, frame assembly 102 can arrange optical signal transmission fibers in an optimum optical pathway orientation. In some embodiments, frame assembly 102 provides for controlled orientation of optical transmission fibers 116 between the fins of a heat sink to a detection area.

Optical transmission fibers 116 are optical signal transmission conduits between interface plate 106 and base 112 of frame assembly 102. In some embodiments, each optical transmission fiber 116 is a multicore fiber having a plurality of flexible, transparent cores 118 that transmit light between the two ends of the optical transmission fiber 116. Transparent cores 118 can be made of glass (silica) or polymer.

Figure 2:
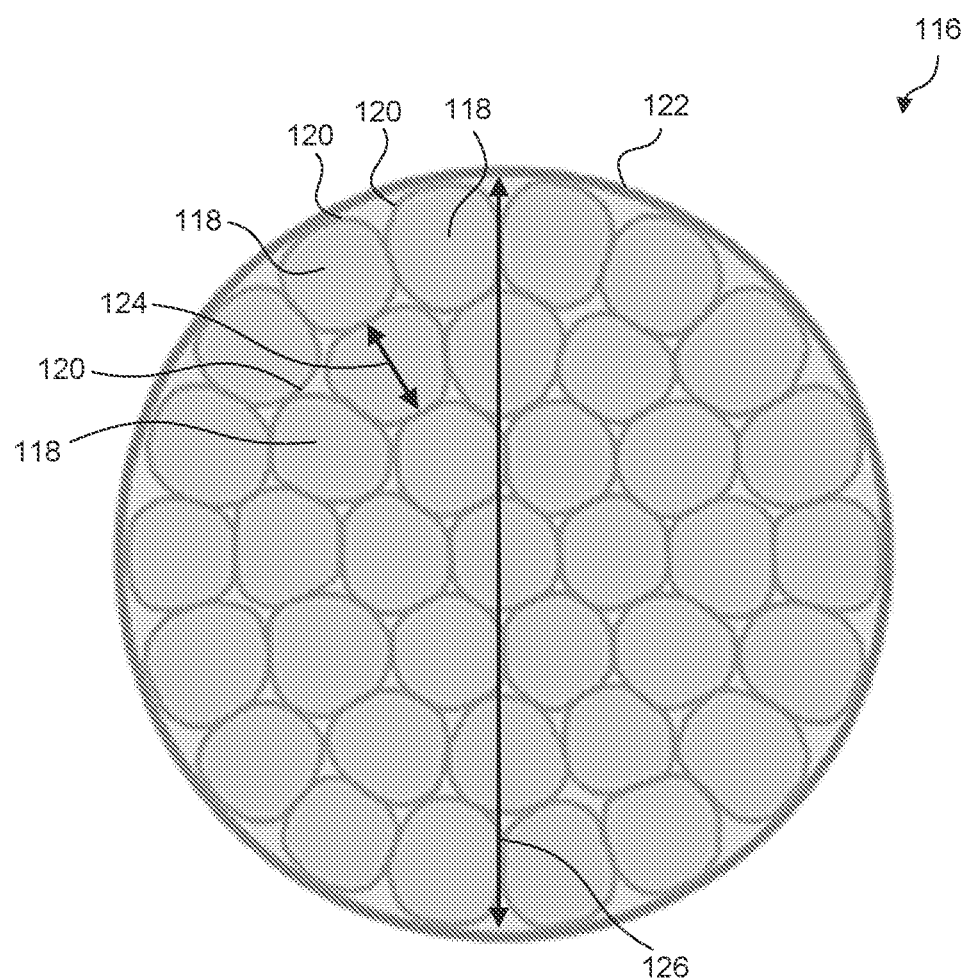
FIG. 2 is a cross-sectional view of a signal transmission fiber, according to an embodiment.

FIG. 2 illustrates a cross-section of an exemplary multi-core optical fiber 116 according to an embodiment. In some embodiments (as shown in FIG. 2), each core 118 includes an optical cladding 120 that encases core 118, and a jacket 122 encases the plurality of cores 118, thereby forming optical transmission fiber 116.

In some embodiments, a diameter 124 of each core 118 ranges from about 500 µm to about 2500µ. For example, diameter 124 can be about 1500 µm. In other embodiments, diameter 124 is less than about 500 µm or more than about 2500 µm.

In some embodiments, a diameter 126 of the entire optical fiber 116 ranges from about 1000 µm to about 3500 µm. For example, diameter 126 can be about 2200 µm. In other embodiments, diameter 126 is less than about 1000 µm or more than about 3500 µm.

In some embodiments, each optical transmission fiber 116 includes at least 10 cores 118. For example, as shown in FIG. 2, optical transmission fiber 116 can include thirty-seven cores 118. In other embodiments, optical transmission fiber 116 includes ten to thirty-six cores 118 or more than thirty-seven cores 118.

In some polymer embodiments, each core 118 is made of polymethyl methacrylate (PMMA), also referred to as acrylic. In other polymer embodiments, cores 118 are made of any other suitable polymer.

In some embodiments, optical cladding 120 is made of any suitable fluorinated polymer. For example, cladding 120 can be made of an opaque or transparent material having a lower index of refraction than the material composing cores 118. In some embodiments, cladding 120 is made of a material that is resistant to the effects of high heat indexes—the optical transmission properties of cores 118 are maintained in the presence of heat indexes well-above room temperature.

In some embodiments, jacket 122 is made of polyethylene (PE) or any other suitable polymer.

In some embodiments, the numerical aperture (NA) of each core 118 ranges from about 0.25 to about 0.75. In some embodiments, the numerical aperture is about 0.5. In other embodiments, the numerical aperture is less than about 0.25 or more than about 0.75.

In some embodiments, the attenuation of each optical transmission fiber 116 is equal to or less than about 0.5 dB/m. For example, the attenuation is equal to or less than 0.45 dB/m. In other embodiments, the attenuation of each optical transmission fiber 116 is more than 0.5 dB/m.

In some embodiments, the minimum bend radius of each optical transmission fiber 116 is equal to or less than about 15 mm. For example, the minimum bend radius can be about 10 mm or about 5 mm, or the minimum bend radius is equal to or less than about 5 mm. In other embodiments, the minimum bend radius is more than about 15 mm.

In some embodiments, the minimum bend radius ranges from about 1.75 times to about 2.75 times the diameter 126 of optical transmission fiber 116. For example, the bend radius can be about 2.25 times the diameter 126 of optical transmission fiber 116. In other embodiments, the minimum bend radius is less than 1.75 times the diameter 126 or more than 2.75 times the diameter 126.

In some embodiments, each core 118 can have a non-circular cross-section. For example, as shown in FIG. 2, one or more of cores 118 can have a substantially trapezoidal cross-sectional shape. Non-circular cross-sections can be achieved, for example, by placing cores 118 together at higher temperatures and under pressure during the manufacturing process of optical transmission fiber 116. In some embodiments, the non-circular cross-section minimizes the space between adjacent cores 118.

In some embodiments, the relative position of each core 118 at one end of fiber 116 is the same as the relative position of each core 118 at the other end of fiber 116. That is, the spatial core arrangement at one end of each fiber 116 is the same as the spatial core arrangement at the other end of fiber 116. In such embodiments, the spatial distribution of optical intensity of the light is not mixed or homogenized as the light travels from one end to the other of fibers 116.

In other embodiments (not shown), each core 118 has a circular cross-section.

In some embodiments, fibers 116 are configured to meet the background fluorescence requirements for the fluorescent moieties, for example, fluorescing dyes, being used to perform assays with the sample assay instrument. Background fluorescence is the light emitted by fibers 116, themselves, in response to transmitting the excitation optical signal. Background fluorescence can create problems if it has the same wavelength as the light emitted by the fluorescent moiety when excited by the same excitation wavelength. Accordingly, in some embodiments, fibers 116 are configured such that magnitude (e.g., in relative fluorescence units (RFU)) of the background fluorescence of fibers 116 at a particular emitted wavelength when excited by an excitation wavelength for a particular fluorescent moiety is below a predetermined threshold. In some embodiments, fibers 116 are also configured such that magnitude (e.g., in relative fluorescence units (RFU)) of the background fluorescence of fibers 116 at a particular emitted wavelength when excited by an excitation wavelength for a particular fluorescent moiety used in an assay is also above a predetermined threshold. For example, in some embodiments, fibers 116 are configured such that the magnitude of background fluorescence that corresponds to the respective emitted wavelengths for the following fluorescing dyes falls within the following predetermined maximum and minimum thresholds:

|  | FAM | HEX | ROX | DY647 | DY677 |
| --- | --- | --- | --- | --- | --- |
| MAX. (RFU) | 3500 | 400 | 200 | 750 | 750 |
| MIN. (RFU) | 500 | 40 | 30 | 30 | 30 |

Turning back to FIG. 1, frame assembly 102 is configured to reconfigure or reformat the relative spatial arrangements of optical transmission fibers 116 at first ends relative to their second ends. In some embodiments, frame assembly 102 is configured to rearrange optical transmission fibers 116 into a spatial fiber arrangement in which they can be more efficiently interrogated by a signal measuring device that measure signals transmitted through each fiber 116. In the context of this description, the first end of a respective fiber 116 corresponds to the end of fiber 116 closest to the signal emission source that is being measured, and the second end of the respective fiber 116 corresponds to the end of fiber 116 closest to the signal detector. The labels "first" and "second" ends is merely a convenient terminology for distinguishing one end of a respective transmission fiber 116 from another end of the transmission fiber 116. Otherwise, the designation of the ends as being a first end or a second end is arbitrary.

The first ends of transmission fibers 116 are attached to interface plate 106. For example, the first ends can extend into or through holes 128 defined by interface plate 106. In some embodiments, signal coupling elements 130, e.g., ferrules or connectors, may be provided in each of holes 128 defined by interface plate 106. Signal coupling elements 130 are configured to securely attach each optical transmission fiber 116 to interface plate 106. Although not shown in FIG. 1, each hole 128 formed in interface plate 106 may be in signal transmission communication, i.e., optically coupled, with an emission signal source. In some embodiments, a signal emission source may comprise a receptacle containing the contents of a chemical or biological assay (e.g., a sample). The receptacles may be positioned and held so as to optically isolate each receptacle from the surrounding receptacles. In addition, as noted above, the receptacles may be held within an incubator device configured to alter the temperature of receptacles or maintain the receptacles at a specified temperature. In some embodiments, interface plate 106 can be made of a suitable heat-conducting material, such as aluminum or copper, and include a plurality of heat dissipating fins 132 formed on one side of interface plate 106 for dissipating heat from interface plate 106 by convection. In some embodiments, signal coupling elements 130 can thermally insulate optical transmission fibers 116 from the heat of the receptacles held within the incubator. An exemplary insulating material for signal coupling elements 130 includes polyethylene ketone (PEEK).

In some embodiments, optical transmission fibers 116 are attached to interface plate 106 in a rectangular spatial arrangement comprising a plurality of rows, as shown in FIG. 1. Each row can have one or more transmission fibers 116. As shown in the illustrated embodiment, interface plate 106 can include heat dissipating fins 132, and transmission fibers 116 may extend between adjacent fins 132 into an associated hole 128 formed in interface plate 106. In the illustrated embodiment, interface plate 106 forms twelve rows of five transmission fibers 116 each, for a total of sixty transmission fibers 116 that can be employed for interrogating up to sixty individual emission sources (e.g., reaction receptacles containing reaction materials (e.g., a sample) therein). Each row of transmission fibers 116 may be disposed between a pair of adjacent heat-dissipating fins 132.

The second ends of transmission fibers 116 are attached to base 112 of frame assembly 102. The second ends of transmission fibers 116 can be, for example, aligned with or inserted into or through fiber-positioning holes 114. Fiber-positioning holes 114 are spatially arrange differently from the spatial arrangement of fiber-receiving holes 128 formed in interface plate 106. The spatial arrangement of fiber-positioning holes 114 is configured to allow for efficient interrogation by one or more signal detectors. In the illustrated embodiment, the fiber-positioning holes 114 for each signal detector head is arranged in a circle. As shown in FIG. 1, each circular spatial arrangement accommodates a plurality of transmission fibers 116 extending from interface plate 106. Other spatial arrangements are contemplated, including, two or more concentric circles, one or more open rectangles, one or more ovals, etc.

The length of the frame assembly 102 is defined by a distance between base 112 and interface plate 106. In some embodiments, this length can be based one or more competing design considerations. On one hand is making signal detection module 100 as compact as possible, which includes making the length of frame assembly 102 as small as possible. On the other hand, the flexibility of transmission fibers 116 is limited by the minimum bend radius of fibers 116. A longer frame assembly 102 will make it easier to bend each transmission fiber 116 when reformatting the fibers from their spatial configuration at interface plate 106 to their spatial configuration at base 112. In one embodiment, when each circular arrangement includes thirty multicore fibers 116 having a minimum bend radius of 5 mm or less, frame assembly 102 can have a length that ranges from about 100 mm to about 300 mm. For example, the length of frame assembly 102 can be about 130 mm to about 160 mm.

Figure 3:
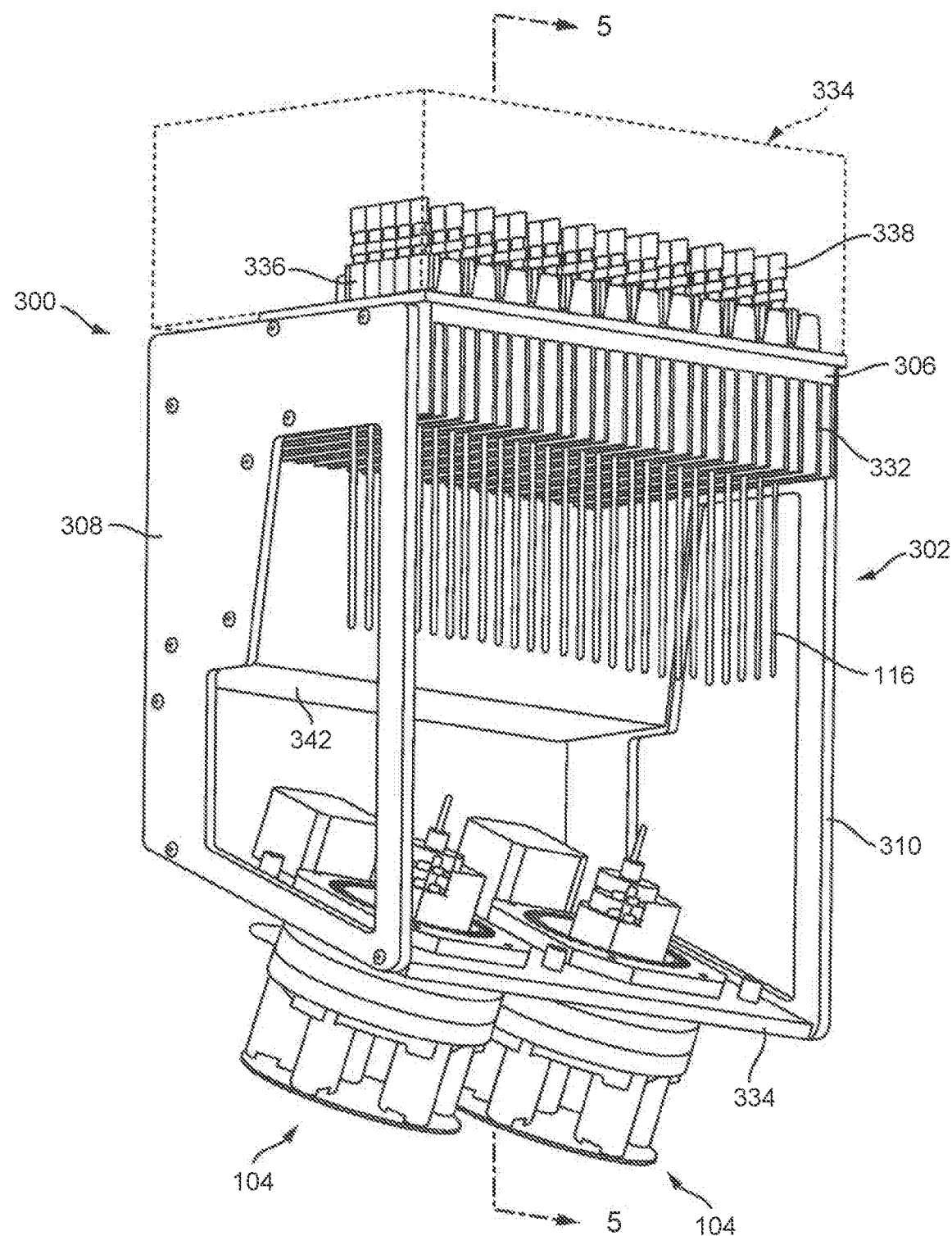
FIG. 3 is a front perspective view of a signal detection module, according to an embodiment.
Figure 4:
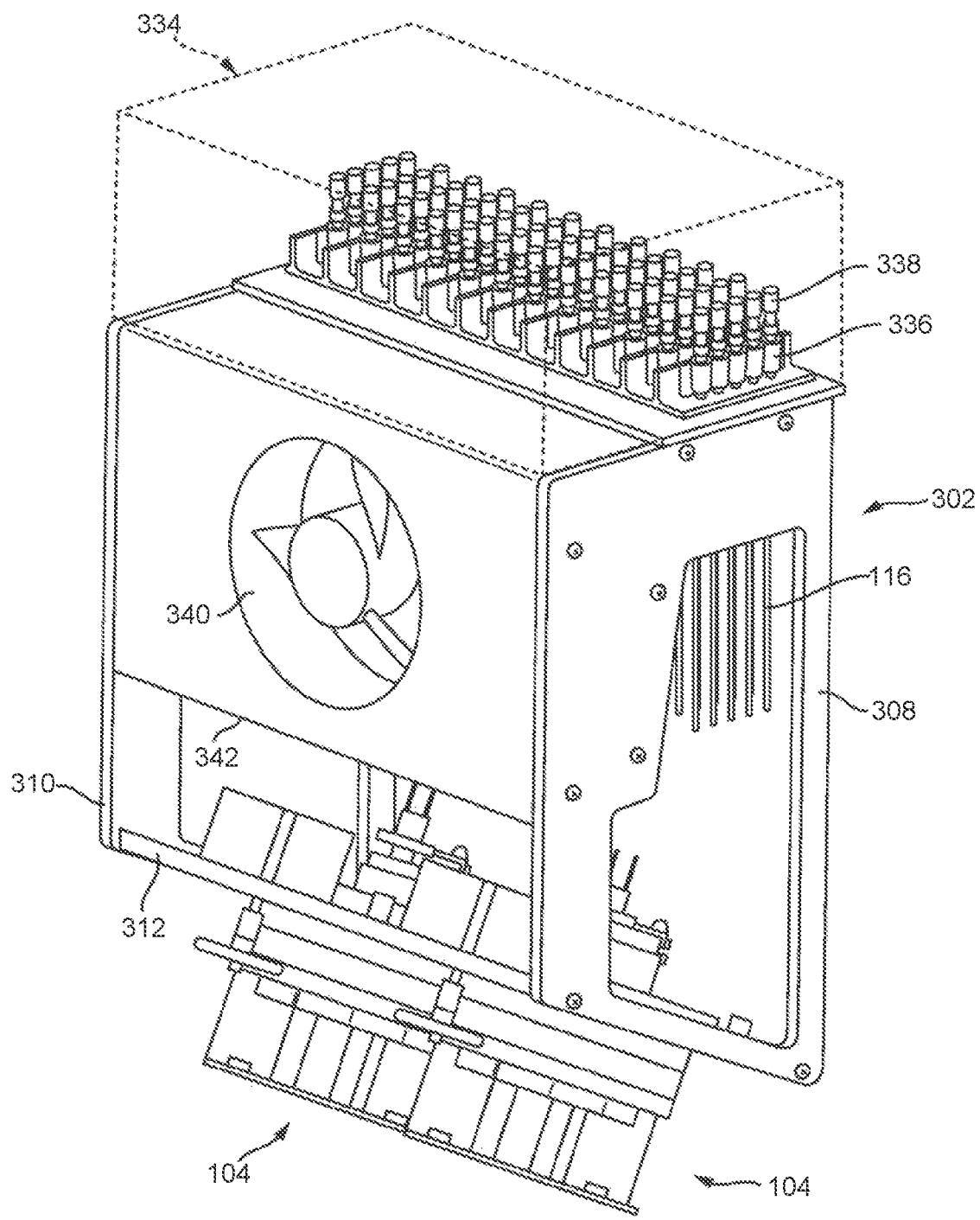
FIG. 4 is a rear perspective view of the signal detection module shown in FIG. 3, according to an embodiment.
Figure 5:
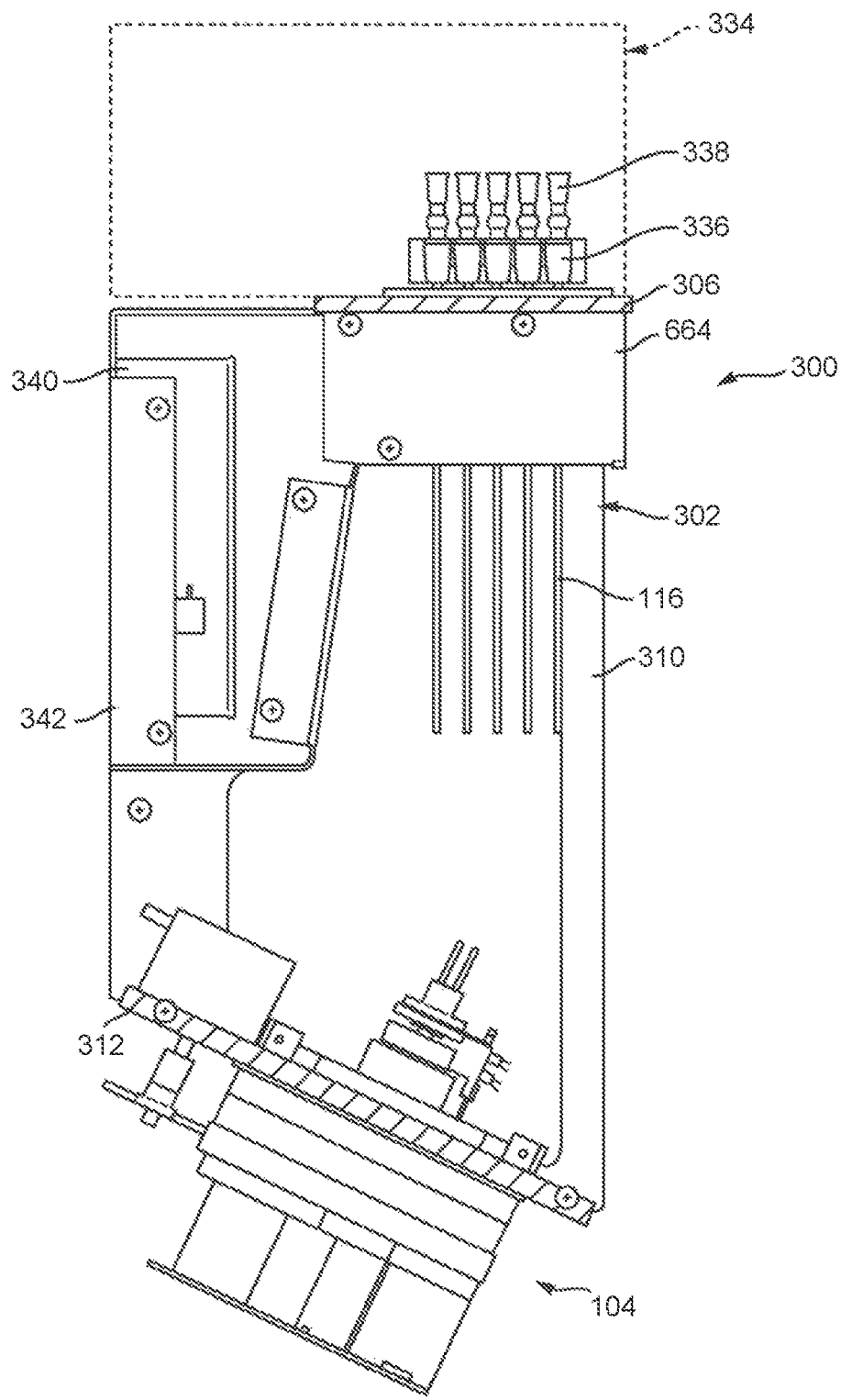
FIG. 5 is a cross-sectional view of the signal detection module along the line 5-5 in FIG. 3, according to an embodiment.

FIGS. 3-5 illustrate an alternative embodiment of a signal detection module 300. Signal detection module 300 can include a frame assembly 302 that includes sides 308, 310. Frame assembly 302 can also include a base 312, and an interface plate 306 attached to one end of frame assembly 302. Signal detection module 300 can also include two signal detector heads 104 attached to base 312 at an end of frame assembly 302 opposite of interface plate 306. As opposed to the embodiment shown in FIG. 1, in which base 112 of frame assembly 102 forms a generally orthogonal angle with respect to the sides 108, 110 of frame assembly 102 such that base 112 is generally parallel to interface plate 106, frame assembly 302 of signal detection module 300 is configured such that base 312 is angled relative to interface plate 306 so that base 312 is not parallel to interface plate 306.

Optical transmission fibers 116 extend from a first end thereof connected to interface plate 306 to a second end thereof connected to base 312. Optical transmission fibers 116 at the first end have a first spatial fiber arrangement, and have a second spatial fiber arrangement, different than the first spatial fiber arrangement, at the second end. As with the embodiment shown in FIG. 1, transmission fibers 116 can be reformatted from a generally rectangular, multi-row arrangement at interface plate 306 into two circular arrangements, each accommodating half of transmission fibers 116, at base 312.

As also shown in FIGS. 3-5, a processing module 334, such as an incubator (e.g., a thermocycler), is positioned above interface plate 306. Processing module 334 can include a plurality of receptacle holders 336, each configured to hold one or more receptacles 338. In the illustrated embodiment, receptacle holders 336 are configured to collectively hold sixty receptacles 338 arranged in twelve rows of five receptacles 338 each. The arrangement of receptacle holders 336 (and receptacles 338 supported thereby) corresponds to the spatial arrangement of the first ends of fibers 116 at interface plate 106. Accordingly, the first ends of fibers 116 can be optically coupled with receptacles 338. In some embodiments, receptacle holders 336 are configured to collectively hold less than or more than sixty receptacles 338. In some embodiments, processing module 334 may be an incubator, and each receptacle holder 336 is configured to impart thermal energy to receptacles 338 held thereby to change and/or maintain the temperature of the contents of each receptacle 338.

For applications in which heat dissipation from interface plate 306 is necessary or desirable, such as when the processing module 334 includes an incubator or other heat-generating device, heat dissipating fins 332 may be provided on interface plate 306. To augment heat dissipation via heat dissipating fins 332, signal detection module 300 may include a fan 340 (shown in FIGS. 4 and 5) disposed within a fan housing 342 mounted to frame assembly 302. Fan 340 is configured to generate air flow over heat dissipating fins 332 to enhance the convective heat dissipation from fins 332.

Figure 7:
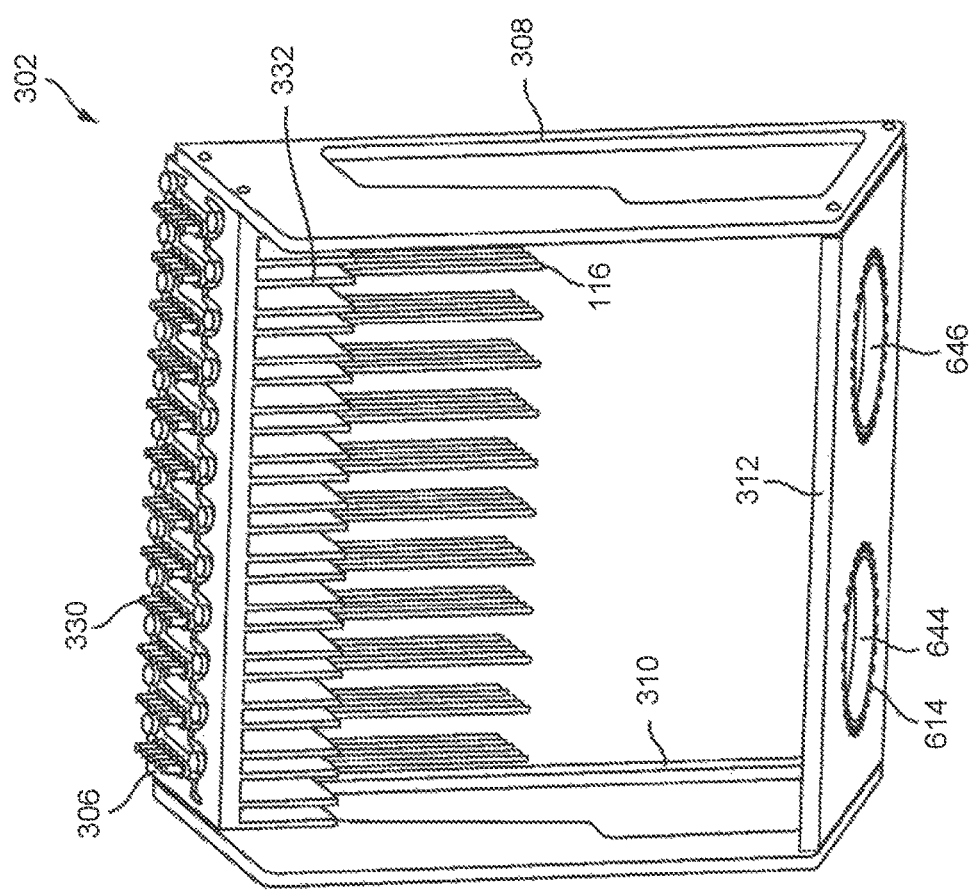
FIG. 7 is a rear perspective view of the frame assembly shown in FIG. 6, according to an embodiment.
Figure 6:
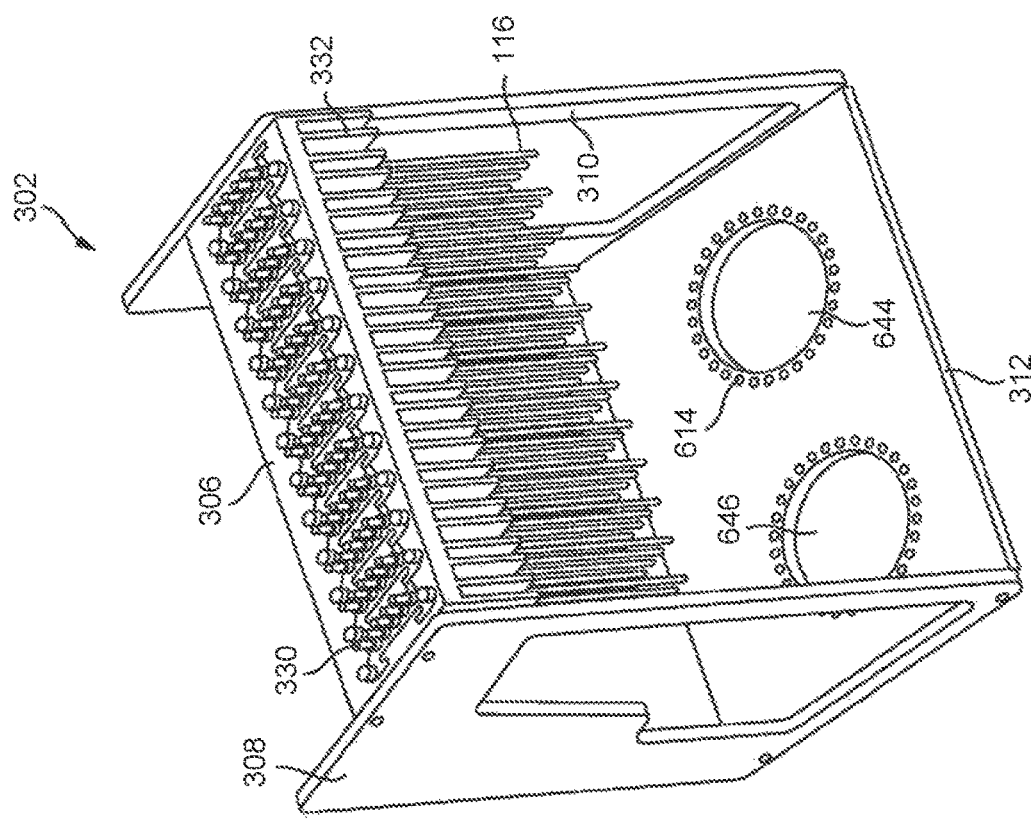
FIG. 6 is a front perspective view of a frame assembly of the signal detection module shown in FIGS. 3-5, according to an embodiment.

FIGS. 6 and 7 show a front perspective view and a rear perspective view, respectively, of fiber frame assembly 302 of signal detection module 300 shown in FIGS. 3-5. Signal detector heads 104, processing module 334, fan 340, and fan housing 342 are not shown in FIGS. 6 and 7. As shown in FIGS. 6 and 7, frame assembly 302 includes sides 308, 310, a base 312 attached to one end of sides 308, 310, and an interface plate 306 attached to an opposite end of sides 308, 310. Signal coupling elements 330 are attached to each of the fiber-receiving openings formed in interface plate 306. As explained above, coupling elements 330, which may comprise ferrules or connectors, are constructed and arranged to couple an optic signal from the corresponding transmission fiber 116 to an object to be interrogated adjacent coupling elements 330, such as the contents of a receptacle, and/or couple an optical emission from the object into the transmission fiber 116.

Base 312 can include two openings 644, 646, each configured to accommodate one of signal detector heads 104. A plurality of fiber-positioning holes 614 is provided around each of openings 644, 646. FIGS. 6 and 7 show only a portion of each of transmission fiber 116 extending from interface plate 306. In the illustrated embodiment, transmission fibers 116 are connected to interface plate 306 in a rectangular, multi-row arrangement, and the fiber-positioning holes 614 formed in base 312 are in a circular arrangement so as to reformat transmission fibers 116 from the rectangular arrangement at the first ends of fibers 116 to a circular arrangement at the second ends of fibers 116.

Figure 8:
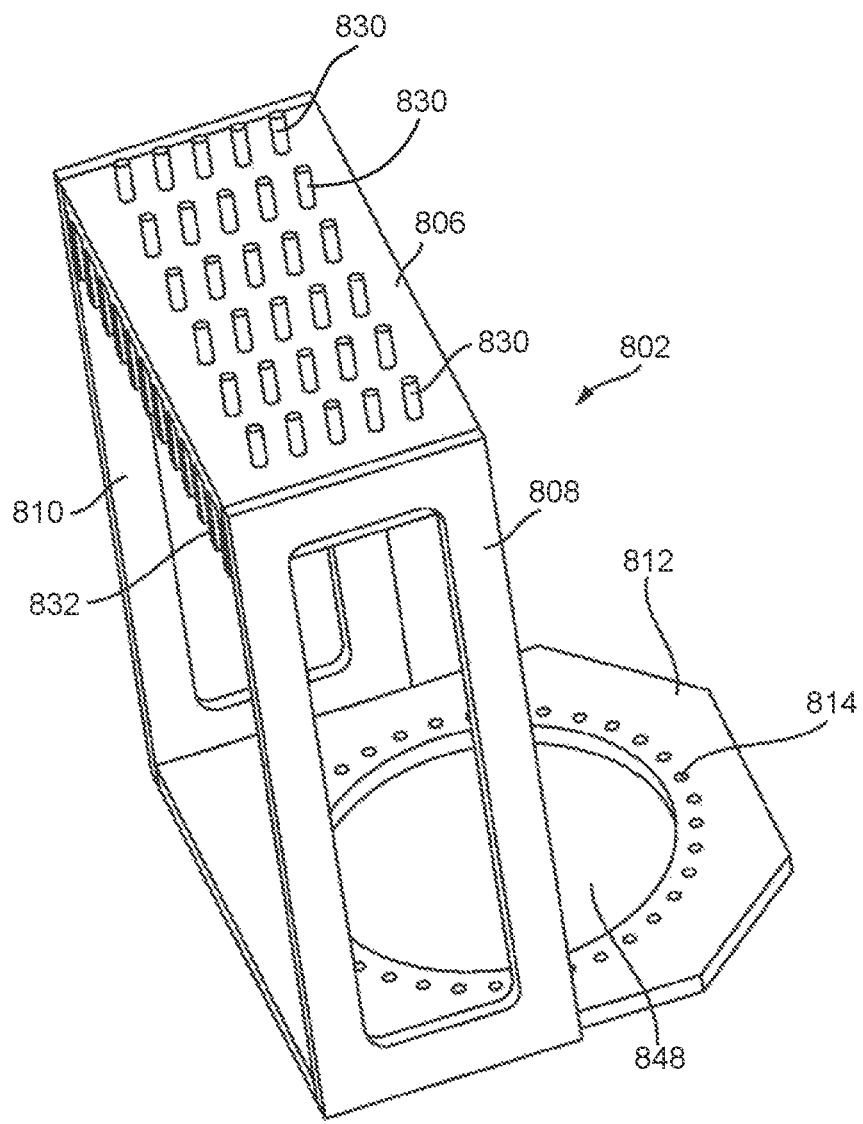
FIG. 8 is a top perspective view of a frame assembly, according to an embodiment.

FIG. 8 is a perspective view of an embodiment of a frame assembly 802. Frame assembly 802 can include sides 808, 810 and a base 812 having an opening 848 formed therein with a plurality of fiber-positioning holes 814 positioned around opening 848 in a generally circular configuration. An interface plate 806 is attached to sides 808, 810 of frame assembly 802 at an end thereof and opposite base 812. Interface plate 806 includes a plurality of coupling elements 830, e.g., ferrules or connectors, and may include heat dissipating fins 832 disposed on a side of interface plate 806 opposite coupling elements 830. Each coupling element 830 corresponds to a fiber-receiving opening formed through interface plate 806. As can be seen in FIG. 8, coupling elements 830 are arranged in a rectangular, multi-row arrangement of six rows of five coupling elements 830 each. The number of openings 814 formed in base 812 can correspond to the number of coupling elements 830 formed in the interface plate 806. Thus, it can be appreciated that the frame assembly 802 shown in FIG. 8 can have half the capacity of frame assembly 102 shown in FIG. 1 (in some embodiments), and frame assembly 102 corresponds essentially to a doubling of frame assembly 802 with a second opening 848 and corresponding fiber-positioning holes 814 surrounding opening and six additional rows of five coupling elements 830 attached to interface plate 806. Frame assembly 802 could be configured to have the same capacity, or more or less capacity to that of frame assembly 102 shown in FIG. 1.

Figure 9:
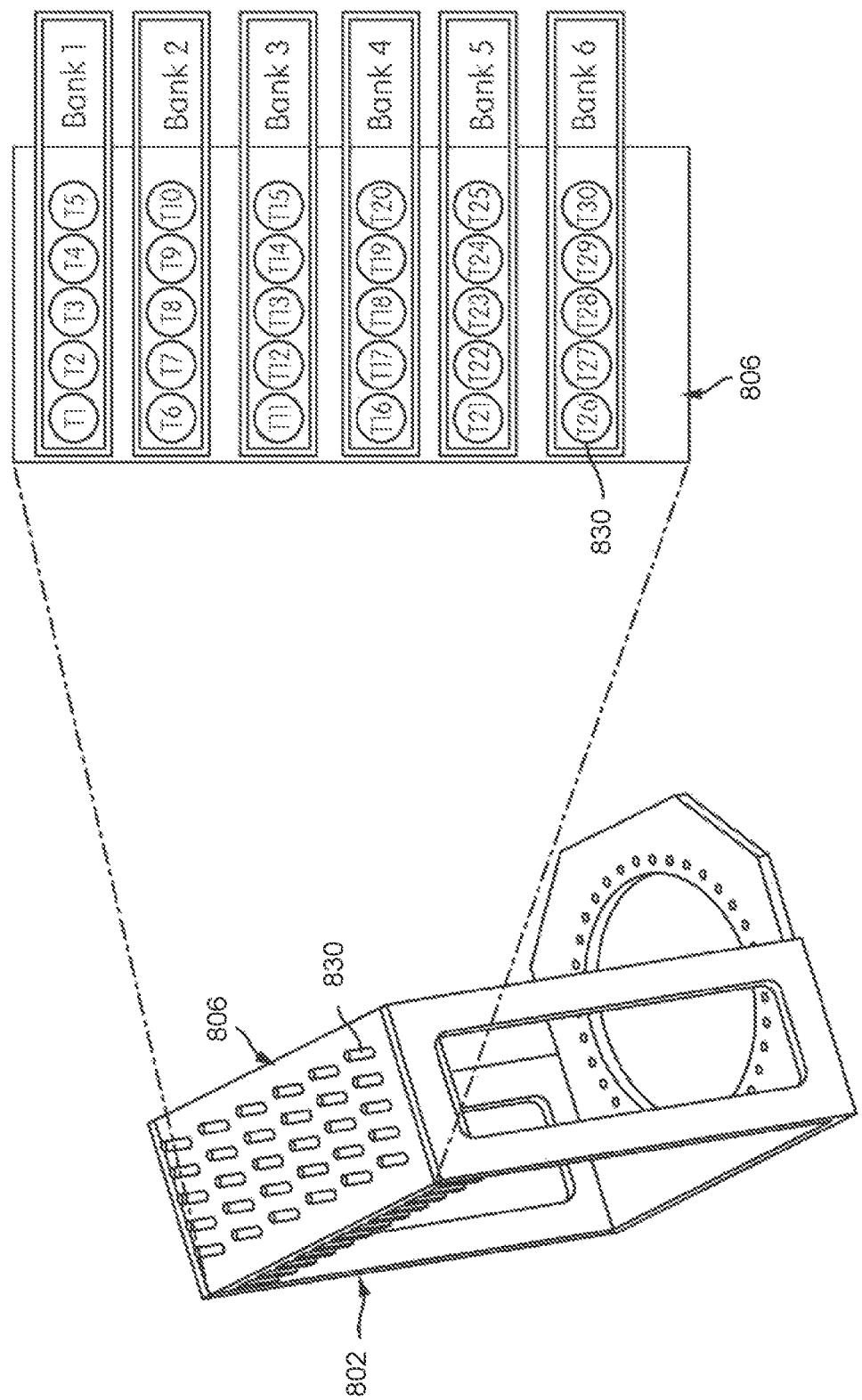
FIG. 9 shows the fiber position mapping at an interface plate of the frame assembly shown in FIG. 8, according to an embodiment.

FIG. 9 shows an exemplary mapping of the spatial arrangement of fiber positions at interface plate 806 of the frame assembly 802. As shown in FIG. 9, interface plate 806 includes six rows, or banks, of five fiber positions each, designated T1-T5, T6-T10, T11-T15, T16-T20, T21-T25, and T26-T30.

Figure 10:
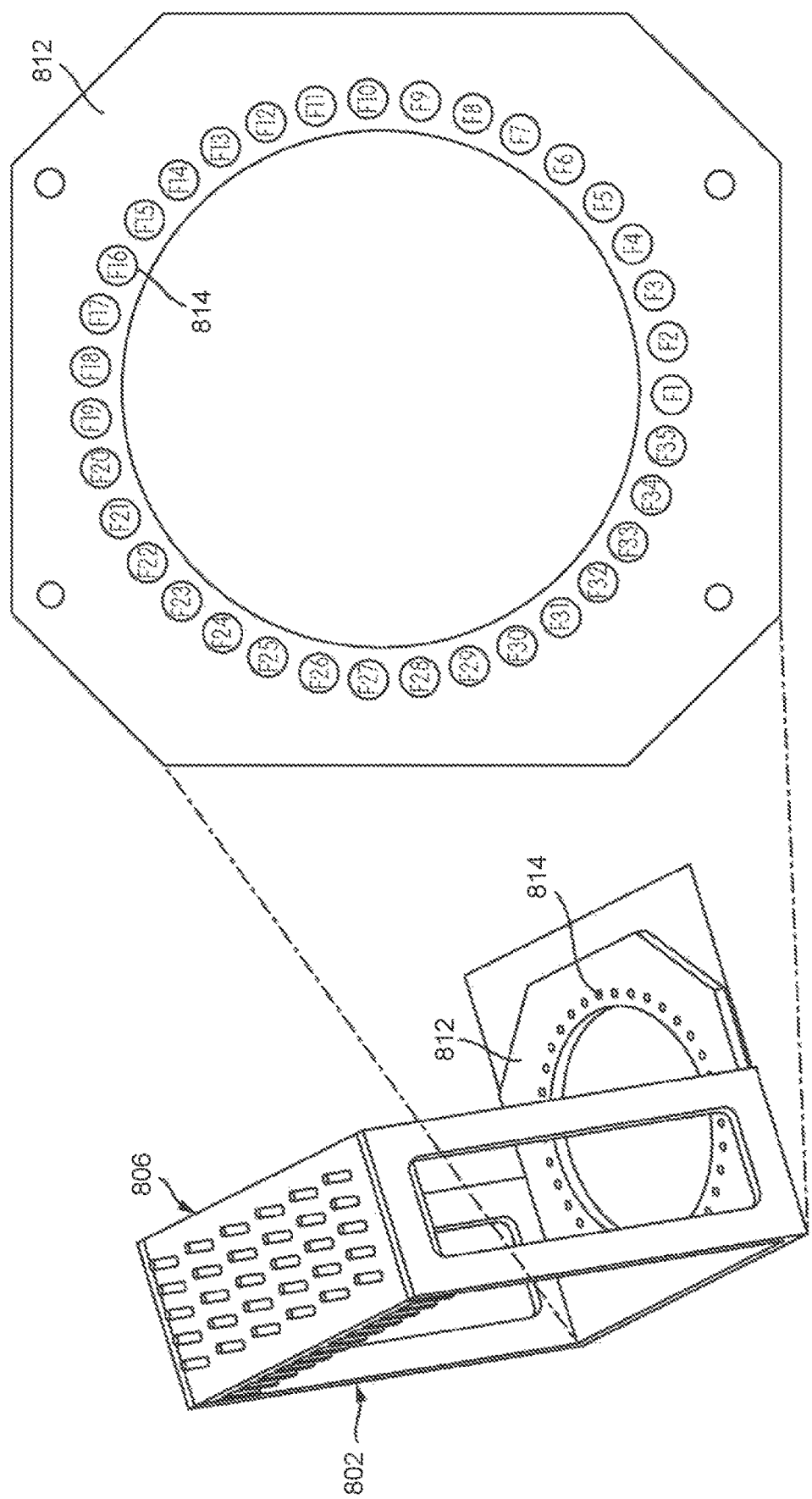
FIG. 10 shows the fiber position mapping at a baseplate of the frame assembly shown in FIGS. 8 and 9, according to an embodiment.

FIG. 10 shows an exemplary mapping of the spatial arrangement of fiber positions of fiber-positioning holes 814 formed in base 812 of frame assembly 802. In the illustrated embodiment, 35 fiber-positioning holes 814 are formed in the base 812, and are designated F1, F2, F3, F4, . . . F35, starting at the lower (six o'clock) position with respect to the opening 848.

FIG. 11 is a table showing an exemplary mapping of the rectangularly-arranged interface positions T1-T30 in interface plate 806 to thirty of the circularly-arranged fiber-positioning hole positions F1-F35 in base 812. This is exemplary only; other mappings between the fiber positions in interface plate 806 and the fiber positions in base 812 are contemplated. In this embodiment, the number of interface positions in interface plate 806 is exceeded by the number of fiber-positioning holes in base 812 (e.g., 30 vs. 35). Fluorescent calibration targets can be placed in the additional fiber-positioning holes in the base to test and/or calibrate the signal detectors of signal detector head 104.

Figure 12:
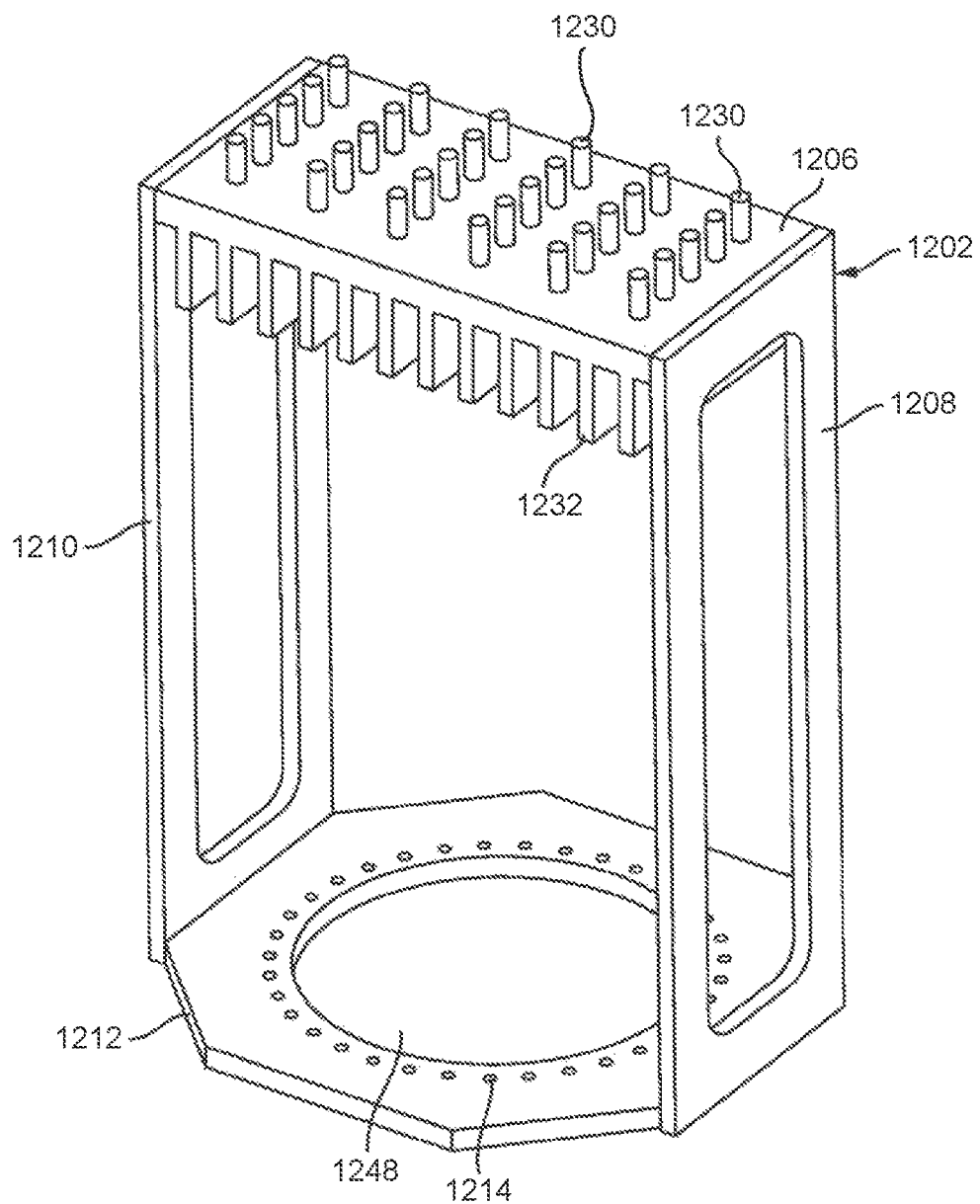
FIG. 12 is a front perspective of a frame assembly, according to an embodiment.

FIG. 12 shows another embodiment of a thirty-fiber frame assembly 1202, including sides 1208, 1210, a base 1212 with an opening 1248, fiber-positioning openings 1214 surrounding opening 1248, and an interface plate 1206 having coupling elements 1230 and heat dissipating fins 1232 connected to an end of the frame assembly 1202 opposite base 1212. Frame assembly 1202 is comparable to the frame assembly 802 shown in FIG. 8 and accommodates thirty transmission fibers (not shown in FIG. 12) configured at the first ends thereof at interface plate 1206 in a rectangular arrangement of six rows of five fibers each, and configured at the second ends thereof at base 1212 in a circular arrangement disposed within the fiber-positioning holes 1214 surrounding opening 1248. Frame assembly 1202 shown in FIG. 12 differs from frame assembly 802 shown in FIG. 8 in that base 1212, opening 1248, and fiber-positioning openings 1214 are substantially centered with respect to interface plate 1206. In frame assembly 802 shown in FIG. 8, on the other hand, base 812, opening 848, and fiber-positioning openings 814 are laterally offset with respect to the center of interface plate 806.

In some embodiments, the frame assembly (e.g., frame assemblies 102, 302, 802, and 1202) and multicore fibers 116, according to any of the above described embodiments, are collectively configured such that the variation of the normalized detected intensities among all fibers 116 at each predetermined excitation wavelength of interest is less than or equal to about ±20%. Relative to similar frame assemblies using single core fibers, this variation can be an improvement of about a 40% to 55%. For example, one or more of following parameters can be modified to achieve a variation of the normalized detected intensities that is less than or equal to about ±20%:

the length of the frame assembly (e.g., frame assemblies 102, 302, 802, and 1202)—the distance between the base and the interface plate (e.g., a length in the range from about 130 mm to about 160 mm);

the relative position between (a) the fiber-positioning holes (e.g., holes 114, 614, 814, and 1214) of a base (e.g., bases 112, 312, 812, and 1212) of the frame assembly, and (b) the holes (e.g., holes 128) defined by the interface plate that receive signal coupling elements (e.g., signal coupling elements 130); and the minimum bend radius of each multicore fibers 116 (e.g., a minimum bend radius of about 5 mm or less).

Exemplary Signal Detector Heads

Figure 13:
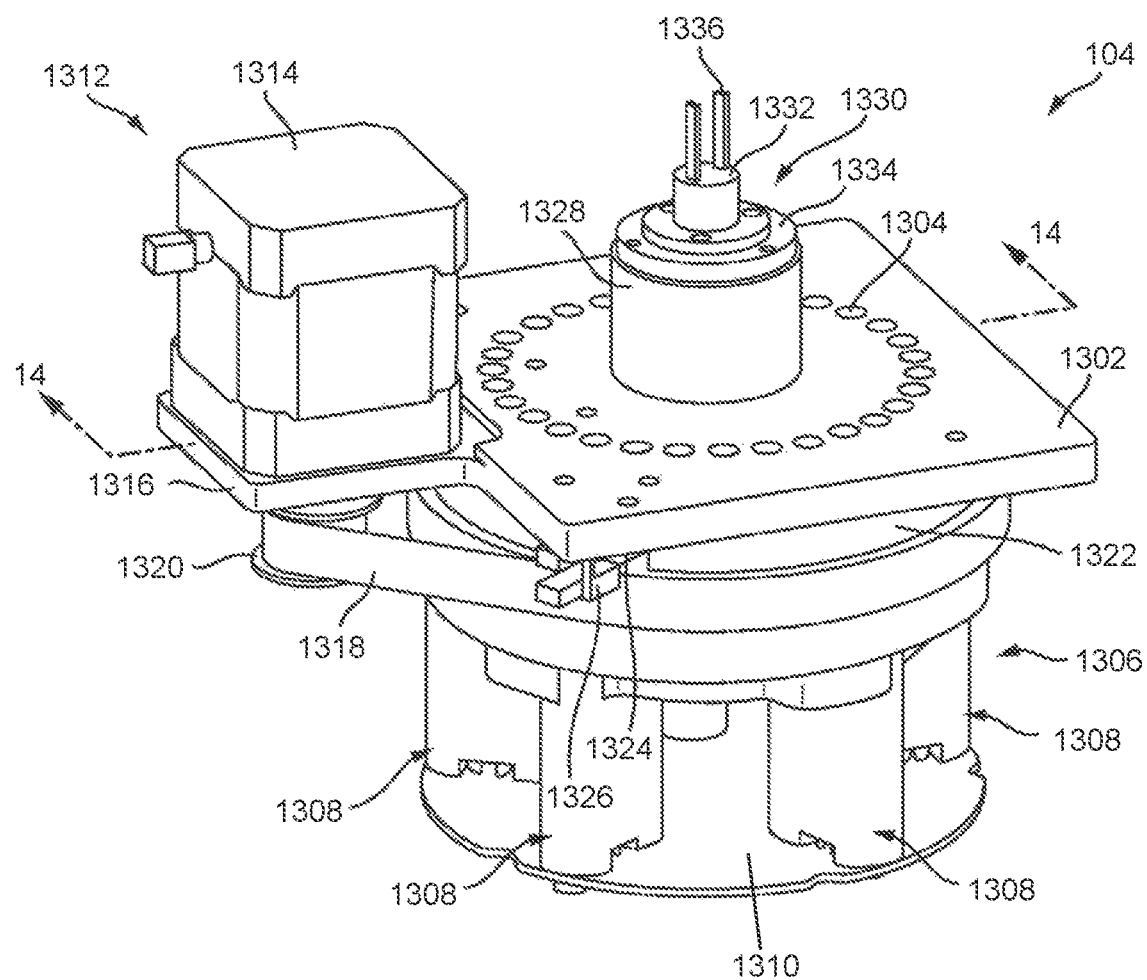
FIG. 13 is a perspective view of a signal detector head, according to an embodiment.

An embodiment of signal detector head 104 is shown in FIG. 13. One or more signal detector heads 104 may be attached to a frame assembly (e.g., frame assemblies 102, 302, 802, and 1202). Signal detector head 104 can be configured to index one or more signal detectors into operative positions with respect to each multicore transmission fiber 116 disposed in a fiber-positioning hole (e.g., holes 114, 614, 814, and 1214) of a base (e.g., bases 112, 312, 812, and 1212) of the frame assembly. That is, signal detector head 104 can be configured to index one or more signal detectors into positions that are optically coupled to the second ends of fibers 116 attached at the base of the frame assembly. Although, signal detector head 104 is configured to be coupled to any frame assembly, including frame assemblies 102, 302, 802, and 1202 described herein, for simplicity of the description, signal detector head 104 will be described in the context of its implementation on frame assembly 102 shown in FIG. 1.

In the embodiment shown in FIG. 13, signal detector head 104 includes a base plate 1302 configured to be attached to base 112 of frame assembly 102. Base plate 1302 can include a plurality of channels 1304 arranged in a configuration corresponding to the spatial arrangement of fiber-positioning holes 114 formed in base 112 of frame assembly 102 so that each channel 1304 will align with a corresponding one of the fiber-positioning holes 114.

In some embodiments, signal detector head 104 can be configured to move one or more signal detectors 1308 to sequentially place each signal detector into an operative position with respect to each transmission fiber 116 to detect a signal transmitted by transmission fiber 116. Signal detector head 104 can also include a movable detector carrier 1306 that moves the signal detectors along a path that corresponds to the spatial fiber arrangement of the second ends of fibers 116 attached at base 112. In the illustrated embodiment, detector carrier 1306 includes a rotating carousel that carries a plurality of signal detectors 1308 in a circular path that corresponds to the circular spatial fiber arrangement of the second ends of fibers 116 attached at base 112. In the illustrated embodiment, signal detector head 104 can include six individual signal detectors 1308. Each signal detector 1308 can be mounted on a printed circuit board 1310, and each signal detector 1308 can be configured to excite and detect a different optical emission signal or an emission signal having different characteristics. In some embodiments, signal detector head 104 includes less than or more than six signal detectors 1308.

As will be described in further detail below, detector carrier 1306 can be configured to move relative to base plate 1302. Signal detector head 104 can also include a detector drive system 1312 configured to power movement, e.g., rotation, of detector carrier 1306. Drive system 1312 can include a drive motor 1314 supported on a motor mount portion 1316 of base plate 1302. A drive belt 1318 is disposed on an output shaft wheel 1320 of motor 1314 and around a pulley wheel 1322 that is attached to or part of detector carrier 1306. Rotation of output shaft wheel 1320 of motor 1314 causes a corresponding rotation of the pulley wheel 1322 and detector carrier 1306 via belt 1318.

The illustrated configuration of detector drive system 1312 is exemplary, and other mechanisms and arrangements may be employed to effect powered movement of detector carrier 1306. For example, output shaft wheel 1320 may comprise an output gear that directly engages gear teeth formed about the outer periphery of pulley wheel 1322, or pulley wheel 1322 could be coupled to the output shaft wheel 1320 indirectly by a gear train comprising one or more intermediate gears between the output shaft wheel (gear) 1320 and pulley wheel 1322. Alternatively, drive motor 1314 could be configured with its rotating output shaft attached concentrically to detector carrier 1306 and its axis of rotation so that rotation of the output shaft by the motor causes a direct corresponding rotation of detector carrier 1306. Other arrangements and configurations for effecting powered movement of detector carrier 1306 will be appreciated by persons of ordinary skill in the art.

In some embodiments, detector carrier 1306 and detector drive system 1312 are configured to rotate detector carrier 1306 in a single direction or in two directions.

Motor 1314 can be a stepper motor and may include a rotary encoder. Detector carrier 1306 may include one or more positional or status feedback sensors. For example, detector carrier 1306 may include a home flag 1324 that is detected by an optical detector 1326 for indicating a rotational "home" position of carrier 1306. Optical detector 1326 may include a slotted optical sensor comprising an optical transmitter and receiver in which the path between the transmitter and receiver is broken by the passage of home flag 1324. Persons of ordinary skill in the art will recognize, however, that other sensors for indicating a home position may be used. Such sensors may comprise proximity sensors, magnetic sensors, capacitive sensors, etc.

A rotary connector transmits data and/or power signals between rotating detector carrier 1306 and signal detectors 1308 carried thereon, and a non-rotating reference environment, such as a controller and power source as described in more detail below. In the illustrated embodiment, base 1302 of signal detector head 104 includes cylindrical housing 1328 projecting upwardly from a planar portion of base 1302, and a slip ring connector 1330 is positioned at an end of cylindrical housing 1328. Slip ring connector 1330 includes a rotating element disposed inside cylindrical housing 1328 and a non-rotating element 1332, attached or otherwise coupled to non-rotating cylindrical housing 1328 by an intermediate ring 1334, to which are attached data and/or power cables 1336. Slip ring connector 1330 transmits data and/or power signals between rotating detector carrier 1306 and signal detectors 1308 carried thereon, and a non-rotating reference environment, such as a controller and power source as described in more detail below.

Figure 14:
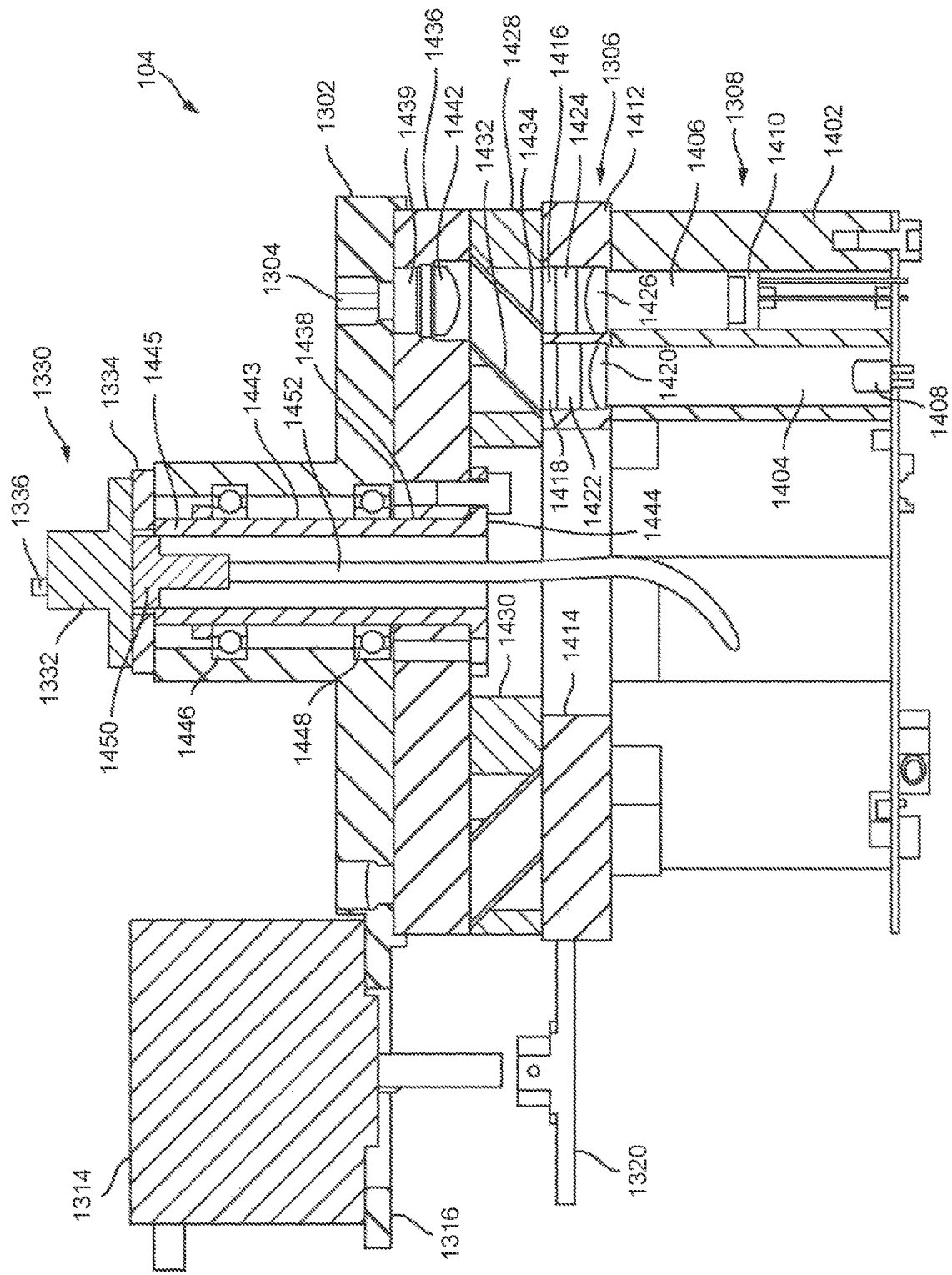
FIG. 14 is a cross-sectional view of the signal detector head along the line 14-14 in FIG. 13, according to an embodiment.

Further details of signal detector head 104 are shown in FIG. 14, which is a cross-sectional view of detector head 104 along the line 14-14 in FIG. 13. Each signal detector 1308 includes a detector housing 1402 within which are formed an excitation channel 1404 and an emission channel 1406, which in the illustrated embodiment are generally parallel to one another. Each signal detector 1308 can include at least one excitation source 1408, such as an LED, is mounted on printed circuit board 1310 at the base of excitation channel 1404. Each signal detector 1308 can include at least one emission detector 1410, such as a photodiode, is coupled to printed circuit board 1310 and is disposed within emission channel 1406.

Detector carrier 1306 can also include, for example, positioned adjacent signal detector housing 1402, a filter plate 1412 having a central opening 1414 formed therein and defining an annulus. Within the annulus, an emission filter opening 1416 and an excitation filter opening 1418 are formed in alignment with emission channel 1406 and excitation channel 1404, respectively, of each signal detector housing 1402. An excitation lens 1420 and an excitation filter 1422 are disposed in excitation opening 1418. Although a single excitation lens 1420 and a single excitation filter 1422 are shown in FIG. 14, signal detector 1308 may include multiple excitation filters and/or multiple excitation lenses. Similarly, an emission filter 1424 and an emission lens 1426 are disposed in emission opening 1416. Although a single emission filter 1424 and a single emission lens 1426 are shown in FIG. 14, the signal detector 1308 may include multiple emission lenses and/or multiple emission filters.

In some embodiments, detector carrier 1306 further includes, for example, adjacent filter plate 1412, a mirror plate 1428 having a central opening 1430 and defining an annulus. The annulus of mirror plate 1428 has formed therein openings aligned with emission opening 1416 and excitation opening 1418 formed in filter plate 1412 for each signal detector 1308. In some embodiments, a mirror 1432 is disposed in mirror plate 1428 in general alignment with excitation channel 1404, and a dichroic filter 1434 is disposed in mirror plate 1428 in general alignment with emission channel 1406. Mirror 1432 can be oriented at an angle (e.g., 45 degrees) with respect to excitation channel 1404 such that it can redirect a light beam.

In some embodiments, detector carrier 1306 further includes an objective lens plate 1436 having a central opening 1438 formed therein and defining an annulus. A lens opening 1440 is formed through the annulus of objective lens plate 1436 in general alignment with emission channel 1406 of each signal detector 1308. An objective lens 1442 is disposed within lens opening 1440.

Base plate 1302 can be disposed adjacent objective lens plate 1436 and can include channels 1304 formed about the perimeter thereof. Although base plate 1302 and objective lens plate 1436 are depicted as abutting one-another in FIG. 14, it is contemplated that there can be a designated distance, forming an air gap, between base plate 1302 and objective lens plate 1436. Also, objective lens plate 1436 and mirror plate 1428 are depicted as abutting one-another in FIG. 14, it is contemplated that there can be a designated distance, forming an air gap, between objective lens plate 1436 and mirror plate 1428.

Detector carrier 1306, having objective lens plate 1436, mirror plate 1428, and filter plate 1412, and signal detectors 1308 carried thereon, are rotatable with respect to base plate 1302 so that each objective lens 1442 associated with each of signal detectors 1308 can be selectively placed into operative alignment (i.e., optically coupled) with one of channels 1304 disposed in base plate 1302. Thus, in the illustrated embodiment having six signal detectors 1308, at any given time, six of channels 1304 are in operative, optical alignment with one of objective lenses 1442 and its corresponding signal detector 1308.

Figure 15:
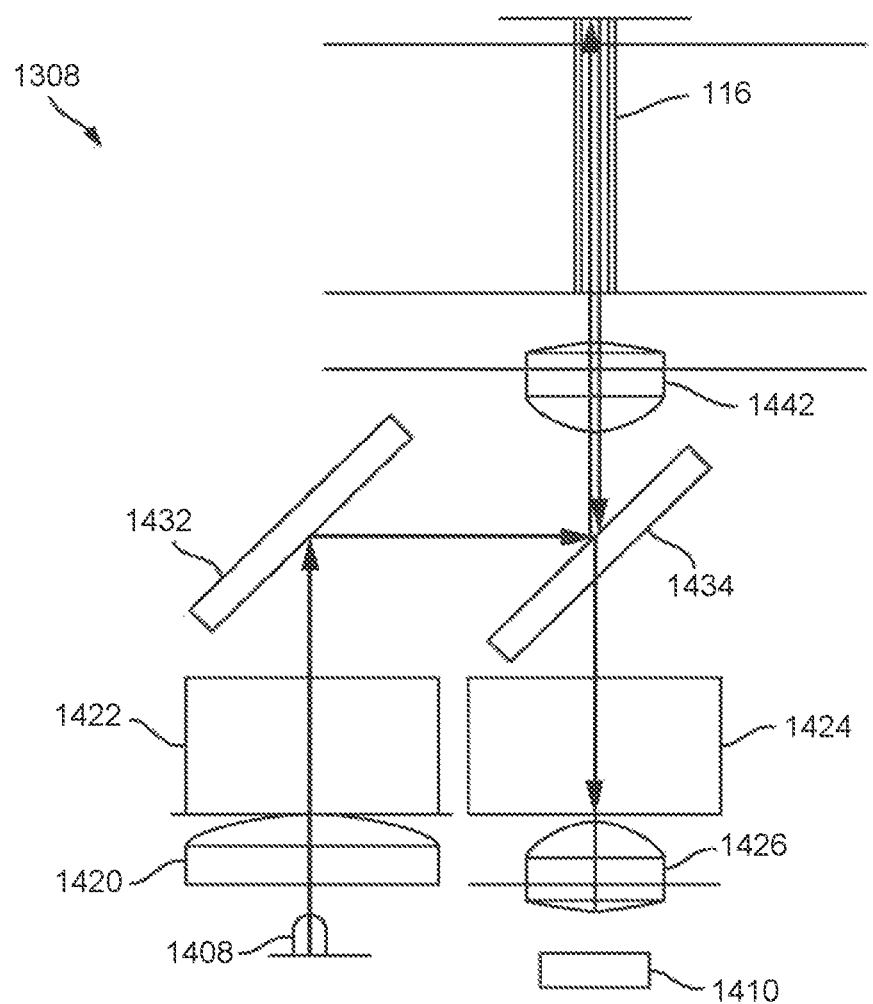
FIG. 15 is a schematic diagram of an exemplary optical path within a signal detector, according to an embodiment.

Operation of signal detector 1308 in an exemplary embodiment is illustrated schematically in FIG. 15. Detector 1308 can be a fluorometer that is configured to generate an excitation signal of a particular, predetermined wavelength that is directed at the contents of a receptacle to determine if a probe or marker having a corresponding emission signal of a known wavelength is present. When signal detector head 104 includes multiple fluorometers 1308 (e.g., six) each fluorometer 1308 is configured to excite and detect an emission signal having a different wavelength to detect a different label associated with a different probe hybridized to a different target analyte. When a more frequent interrogation of a sample is desired for a particular emission signal, it may be desirable to incorporate two or more fluorometers 1308 configured to excite and detect a single emission signal on signal detector head 104.

An excitation signal is emitted by excitation source 1408. Excitation source 1408, as noted above, may be an LED and may generate light at a predetermined wavelength, e.g., red, green, or blue light. Light from source 1408 passes through and is focused by excitation lens 1420 and then passes through excitation filter 1422. Again, FIG. 15 is a schematic representation of signal detector 1308, and the focusing functionality provided by excitation lens 1420 may be affected by one or more separate lenses disposed before and/or after the filter 1422. Similarly, the filter functionality provided by filter 1422 may be affected by one or more individual filters disposed before and/or after one or more lenses 1420 that provide the focusing functionality. Filter 1422 may comprise a low band pass filter and a high band pass filter so as to transmit a narrow wavelength band of light therethrough. Light passing through excitation lens 1420 and excitation filter 1422 is reflected, e.g., laterally, by mirror 1432 toward dichroic filter 1434. Dichroic filter 1434 is configured to reflect substantially all of the light that is within the desired excitation wavelength range toward objective lens 1442. From objective lens 1442, light passes into a transmission fiber 116 and toward the receptacle at the opposite end thereof. The excitation signal is transmitted by transmission fiber 116 to a receptacle so as to expose the contents of the receptacle to the excitation signal.

A label that is present in the receptacle and is responsive to the excitation signal will emit an emission signal. At least a portion of any emission from the contents of the receptacle enters transmission fiber 116 and passes back through objective lens 1442, which focuses the emission light toward dichroic filter 1434. Dichroic filter 1434 is configured to transmit light of a particular target emission wavelength range toward emission filter 1424 and emission lens 1426. Again, the filtering functionality provided by emission filter 1424 may be effected by one or more filter elements and may comprise a high band pass and low band pass filter that together transmit a specified range of emission wavelength that encompasses a target emission wavelength. The emission light is focused by the emission lens 1426, which may comprise one or more lenses disposed before and/or after filter elements represented in FIG. 15 by emission filter 1424. Emission lens 1426 thereafter focuses the emission light of the target wavelength at detector 1410. In one embodiment, detector 1410, which may comprise a photodiode, will generate a voltage signal corresponding to the intensity of the emission light at the prescribed target wavelength that impinges the detector.

Returning again to FIG. 14, a flanged tube 1443 extends through central opening 1438 of objective lens plate 1436 and through cylindrical housing 1328 of base plate 1302. Flanged tube 1443 includes a cylindrical tube 1445 extending through central opening 1438 and cylindrical housing 1328, and a radial flange 1444 disposed within central opening 1430 of mirror plate 1428. Flange 1444 can be secured by suitable fasteners, such as screws or bolts, to objective lens plate 1436. Longitudinally-spaced bearing races 1446, 1448 are disposed between the interior of cylindrical housing 1328 and the exterior of cylindrical tube 1445 of flanged tube 1443. Accordingly, flanged tube 1443 can rotate, with detector carrier 1306, with respect to base plate 1302 and cylindrical housing 1328.

Further details of an exemplary representation of slip ring connector 1330 are also shown in FIG. 14. Slip ring connector 1330 is disposed at the end of cylindrical tube 1445 opposite radial flange 1444. As noted above, cylindrical tube 1445 rotates with detector carrier 1306, while cylindrical housing 1328 remains stationary with base plate 1302. Slip ring connector 1330, which may comprise slip rings and brushes, includes stationary components attached or otherwise coupled to cylindrical housing 1328 and rotating components attached or otherwise coupled to rotating cylindrical tube 1445. Components 1332, 1334 represent non-rotating portion(s) of slip ring connector 1330 in which fixed contact components, such as the brush(es), are located. Component 1450 located inside tube 1445 represents rotating portion(s) of slip ring connector 1330 that rotate with tube 1445 and in which rotating contact elements, such as the ring(s) are located. Cable 1452 represents a power and/or data conductor(s) connecting component 1450 with printed circuit board 1310 and which rotates with the printed circuit board 1310 and signal detector carrier 1306.

As detector carrier 1306 rotates, each of signal detectors 1308 is sequentially placed in an operative position with respect to a second end of a different transmission fiber 116 to interrogate (i.e., measure a signal from) an emission signal source located at a first end of transmission fiber 116. Detector carrier 1306 pauses momentarily at each transmission fiber 116 to permit signal detector 1308 to detect an emission signal transmitted through the transmission fiber 116. Where signal detector 1308 is a fluorometer, detector carrier 1306 pauses momentarily to permit signal detector 1308 to generate an excitation signal of a specified wavelength that is transmitted by transmission fiber 116 to the emission signal source (receptacle) and to detect fluorescence of a specified wavelength excited by the excitation signal that is emitted by the contents of the receptacle and transmitted by the transmission fiber 116 to the fluorometer. Thus, in an embodiment, each transmission fiber 116 can be employed to transmit both an excitation signal and the corresponding emission signal, and each signal detector 1308 can be used to scan multiple transmission fibers and associated emission signal sources.

The emission signal source associated with each transmission fiber 116 is interrogated once by each signal detector 1308 for every revolution of detector carrier 1306. Where signal detector head 104 includes multiple signal detectors 1308 configured to detect different signals, each emission signal source is interrogated once for each different signal for every revolution of detector carrier 1306. Thus, in the case of a nucleic acid diagnostic assay, which may include PCR amplification, the contents of each receptacle is interrogated for each target analyte corresponding to the different probes employed (as indicated by different colored labels) once for each revolution of detector carrier 1306.

In one embodiment, in which base plate 1302 of signal detector head 104 includes thirty (30) fiber channels 1304 for thirty (30) transmission fibers 116, signal detector carrier 1306 rotates one revolution every four (4) seconds, stopping at least ten (10) milliseconds at each fiber channel to measure an emission signal transmitted by the associated transmission fiber 116. Again, if signal detector head 104 includes multiple signal detectors 1308 (e.g., six (6) fluorometers), signal detector head 104 will measure an emission for each of the six different wavelengths of interest once every four (4) seconds. Accordingly, time vs. emission signal intensity data can be generated for each receptacle for each wavelength.

When performing PCR, it is not necessary to synchronize the signal data acquisition with the thermal cycles of the PCR process. That is, it is not necessary that the emission signal of each receptacle be measured at the same temperature point (e.g., about 95° C.) in the PCR cycle. By recording data every four seconds during the entire PCR process, a sufficient number of data points will be collected at each temperature of the PCR thermal cycle. The signal emission data is synchronized with specific temperatures by recording a time stamp for each emission signal measurement and a time stamp for each temperature of the thermal cycling range. Thus, for example, to identify all signal measurements occurring at a temperature of about 95° C., the time stamps of the signal measurements are compared to the temperature time stamps corresponding to a temperature of about 95° C.

The time duration of a thermal cycle is variable, depending on the assay being performed. The minimum time interval is dictated by how fast the thermocycler can ramp temperatures up and down. For a cycler that can ramp the vial filled with fluid from about 55° C. to about 95° C. in about 15 seconds, an exemplary cycle would be anneal at about 55° C. for about 25 seconds, for about 15 second from about 55. ° C. to about 95° C., denature at about 95° C. for 5 seconds, and a 15 second ramp back down from about 95° C. to about 55° C., and then begin another cycle with an about 25 second anneal, Thus, this exemplary anneal-denature cycle would be about a 60 second cycle.

Figure 16:
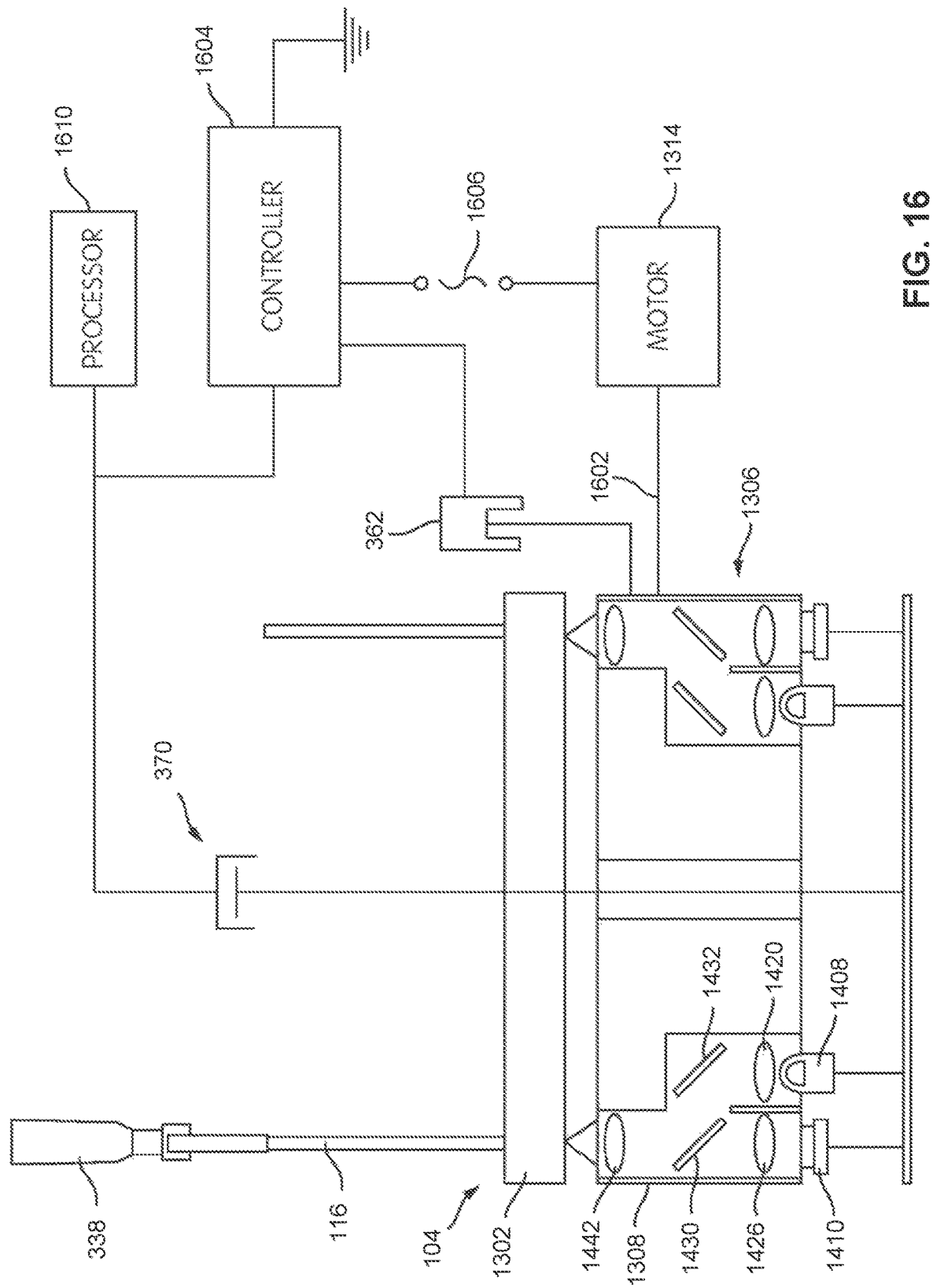
FIG. 16 is a schematic diagram of a signal detection module, according to an embodiment.

The control and data acquisition system of signal detector head 104, according to an embodiment, is shown schematically in FIG. 16. As shown in FIG. 16, detector carrier 1306 carries one or more signal detectors 1308, each of which may, in one embodiment, include an excitation source 1408, an excitation lens 1420, a mirror 1432, a dichroic filter 1434, an objective lens 1442, an emission lens 1426, and an emission detector 1410 as described above. Each receptacle 338 carried in, e.g., a processing module 334 (see FIGS. 3-5), is coupled to a transmission fiber 116 that terminates in base plate 1302 of signal detector head 104. Motor 1314 is mechanically coupled to detector carrier 1306 by a motor coupler 1602 to effect powered movement (e.g., rotation) of detector carrier 1306. A controller 1604 may be coupled to a controllable power source 1606 and to motor 1314 for providing motor control signals and receiving motor position feedback signals, e.g., from a rotary encoder. Controller 1604 may also be coupled to other feedback sensors, such as the home detector 1326 for detecting a rotational position of detector carrier 1306. Controller 1604 also provides controlled power signals, via slip ring connector 1330, to excitation sources 1408 rotatably carried on detector carrier 1306 and coupled to printed circuit board 1310. The functionality of controller 1604 may be provided by one controller or multiple controllers in functional communication with each other. Moreover, one or more controllers, or one or more component(s) thereof, may be carried on the rotating portion of detector head 104, such as on printed circuit board 1310. Voltage signals from the emission detectors 1410, coupled to the printed circuit board 1310, and other data may be carried from detector carrier 1306, via slip ring connector 1330, to a processor 1610 for storing and/or analyzing the data. Alternatively, processor 1610, or one or more component(s) thereof, may be carried on the rotating portion of detector head 104, such as on printed circuit board 1310.

Figure 17:
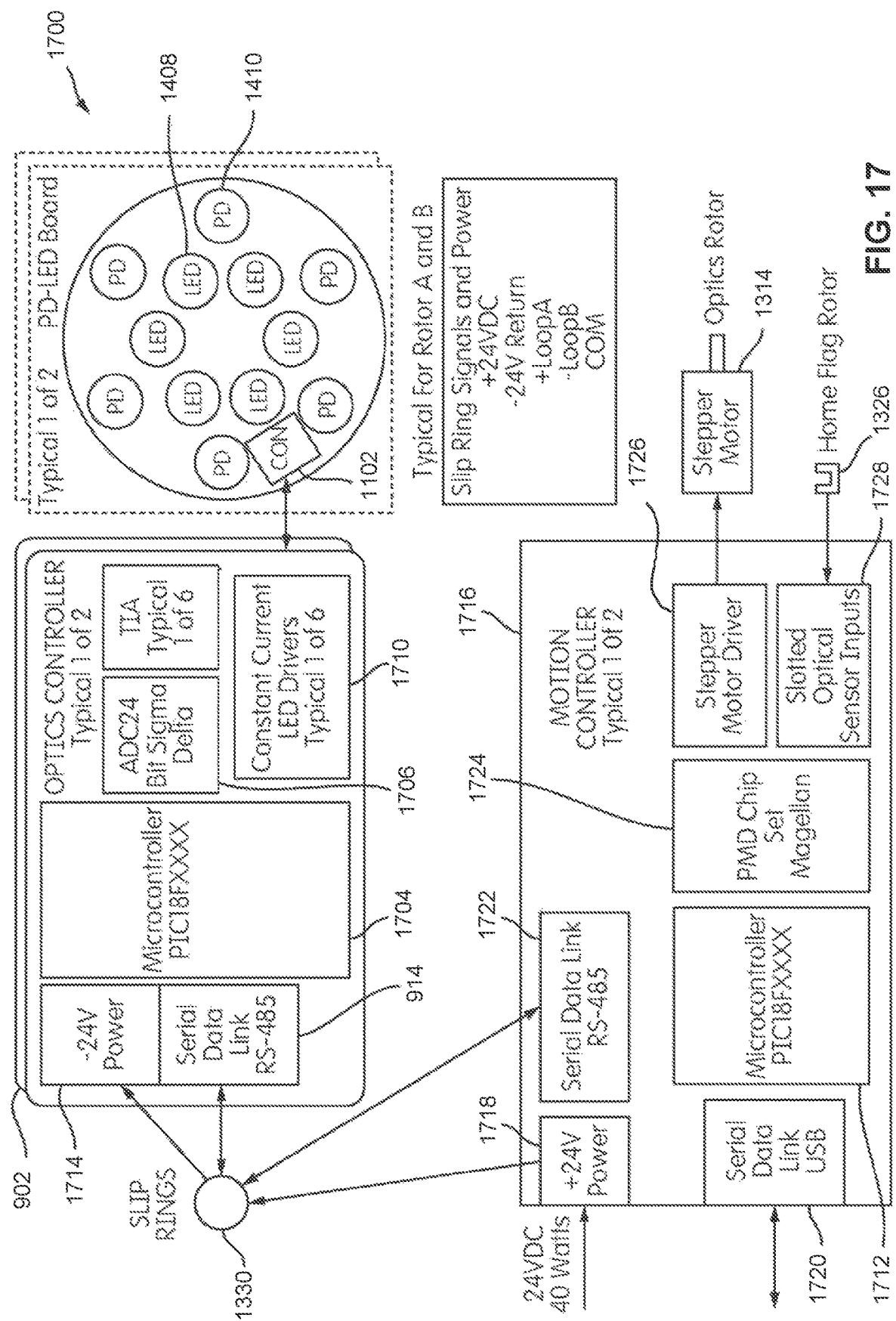
FIG. 17 is a schematic diagram of a control system for a signal detector head, according to an embodiment.

An exemplary control configuration of signal detector head 104 is represented by reference number 1700 in FIG. 17. An optics controller 1702 may be provided for each detector carrier 1306, or rotor, and coupled to printed circuit board 1310 to which the excitation sources (LED) 1408 and emission detectors (e.g., PD (photodiode)) 1410 are attached. Each optics controller 1702 may include a microcontroller 1704, e.g., a PIC18F-series microcontroller available from Microchip Technology Inc., an analog to digital converter 1706, and an integrated amplifier 1708 (e.g., one for each emission detector (PD) 1410). A constant current driver 1710 (e.g. one for each excitation source 1408) is controlled by the microcontroller 1712 and generates control signals (e.g., controlled power) to excitation source 1408. Controller 1702 receives power at point 1714 (e.g., 24 V) from slip ring connector 1330 and can include a serial data link RS-485 914 for commutations between the controller 1702 and slip ring connector 1330.

An exemplary control configuration 1700 may include a motion controller 1716 for each detector drive system 1312 (see FIG. 13). At 1718, motion controller 1716 receives power, e.g., 24 VDC, 40 watts from controllable power source 1606 (see FIG. 15), that is transmitted to optics controller 1702 via slip ring connector 1330. Motion controller 1716 may communicate with an external controller via a serial data link 1720. In one embodiment, controller 1716 communicates with a controller of the thermocycler to synchronize operation of signal detector head 104 with operation of the thermocycler. Controller 1716 may include a serial data link RS-485 1722 for communications between the controller 1716 and slip ring connector 1330. Controller 1716 may further include a microcontroller 1712, e.g., a PIC18F-series microcontroller available from Microchip Technology Inc. and a PMD chip set 1724, which is can be a motor controller to control stepper motor 1314. A stepper motor driver 1726 can be controlled by microcontroller 1712, and generates motor control signals for motor 1314 of optics rotor (i.e., detector drive). A slotted optical sensor input 1728 receives signals from the home flag detector 1326 and communicates such signals to microcontroller 1712.

Figure 18:
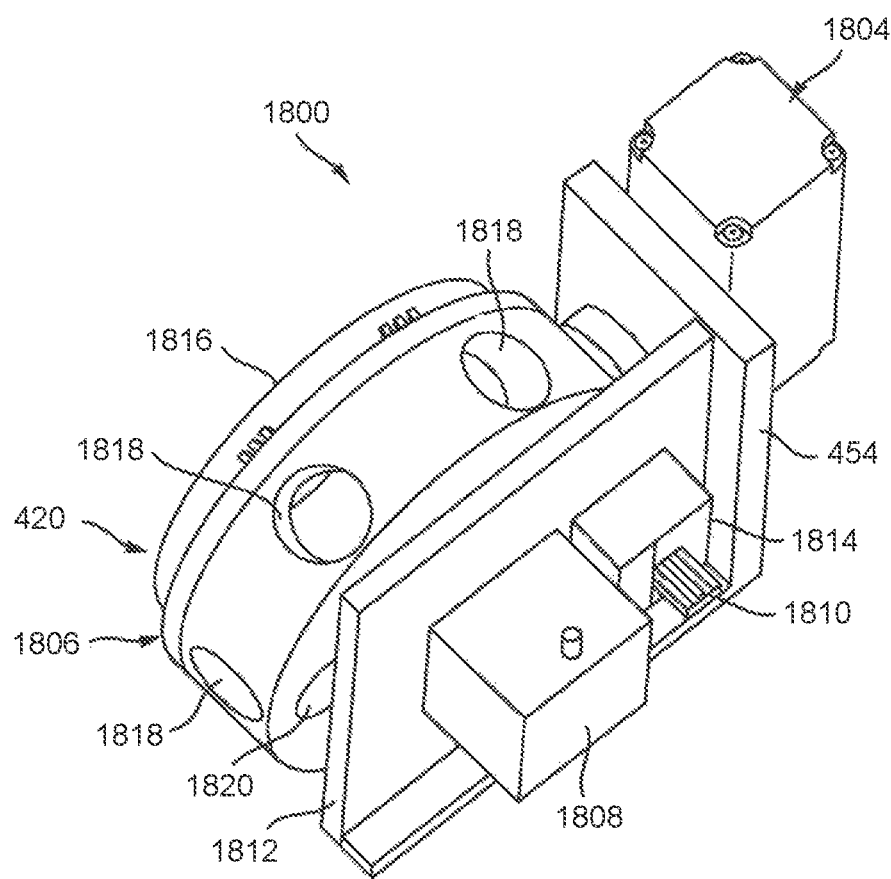
FIG. 18 is a perspective view of a signal detector head, according to an embodiment.
Figure 19:
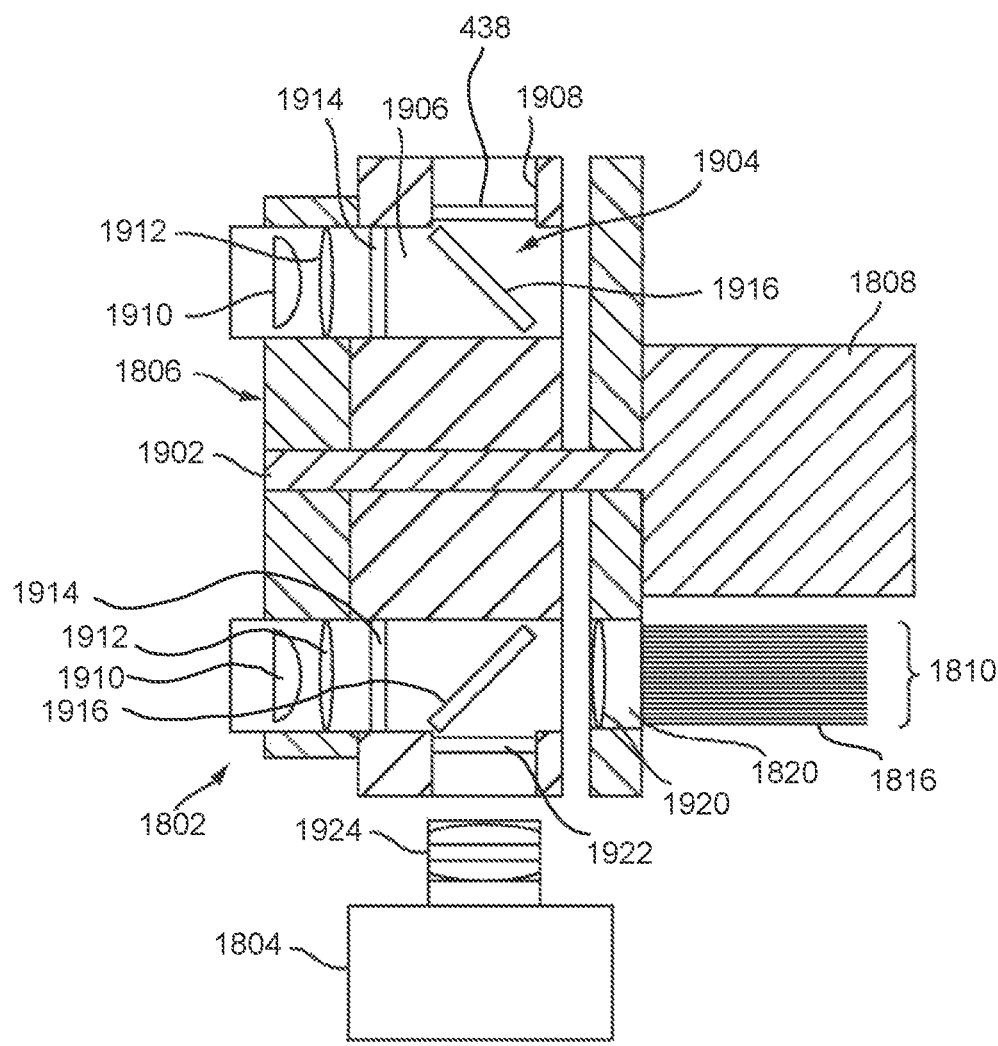
FIG. 19 is a cross-sectional view of the signal detector head of FIG. 18, according to an embodiment.

An alternative embodiment of a signal detector head embodying aspects of the present disclosure is indicated by reference number 1800 in FIGS. 17 and 18. Signal detector head 1800 includes a filter wheel 1802 and a camera 1804 oriented in a radial focal direction with respect to filter wheel 1802. Signal detector head 1800 can employ camera 1804 to image a plurality of bundled fibers 116 to detect a signal transmitted by each fiber 116. Filter wheel 1802 can be indexed to selectively couple each of one or more excitation sources and emission filters with the fiber bundle and camera 1804 to direct an excitation signal of a specified characteristic, e.g., wavelength, to fibers 116 of the fiber bundle and to direct emission signals of a specified characteristic, e.g., wavelength, from fibers 116 of fiber bundle to the camera 1804.

More particularly, signal detector head 1800 includes a filter wheel 1802 that comprises a body 1806. Body 1806 can be configured to rotate about a central axis. Signal detector head 1800 can include a motor 1808 is coupled to filter wheel 1802 by a transmission 1902 to effect powered rotation of filter wheel 1802. Transmission 1902 may comprise any suitable transmission means for transmitting the rotation of motor 1808 to filter wheel 1802. Exemplary transmissions include inter-engaged gears, belts, and pulleys, and an output shaft of the motor 1808 directly attached to body 1806, etc. Motor 1808 may be a stepper motor to provide precise motion control, and may further include a rotary encoder. Filter wheel 1802 may further include a home flag for indicating one or more specified rotational positions of filter wheel 1802. Suitable home flags include slotted optical sensors, magnetic sensors, capacitive sensors, etc. A fiber bundle 1810 includes a plurality of fibers 116 fixed at the first ends thereof with respect to filter wheel 1802, e.g., to a fixed plate 1812 located adjacent to filter wheel 1802, by a fiber mounting block 1814. The second ends of the respective fibers 116 are coupled to respective signal sources positioned in a first specified arrangement, and may include receptacles (such as receptacles 338) positioned in a rectangular arrangement.

Filter wheel 1802 includes one or more optics channels 1904 and is movable so as to selectively index each optics channel 1904 into an operative, optical communication with the fiber bundle 1810 and camera 1804. Each optics channel 1904 includes an excitation channel 1906 formed in an axial direction within body 1806 of index wheel 1802 for transmitting an excitation signal to fiber bundle 1810 and an emission channel 1908 extending radially from excitation channel 1906 to a radial opening on the outer periphery of filter wheel 1802.

An excitation source 1910, e.g., a bright light LED, is disposed within the excitation channel 1906. The excitations sources 1910 of all the emission channels 1908 may be connected to a printed circuit board 1816. One or more lenses 1912 and one or more excitation filters 1914 are positioned within excitation channel 1906 to condition light emitted by source 1910. Each optics channel 1904 may be configured to generate and transmit an excitation signal of a specified wavelength. In such an embodiment, filter(s) 1914 are configured to transmit light at the desired wavelength.

Each channel 1904 includes a dichroic filter 1916 configured to transmit that portion of the excitation signal that is at or near the prescribed excitation wavelength.

When the optics channel 1904 is in optical communication with the fiber bundle 1810—such as by rotating the filter wheel 1802 until optics channel 1904 is aligned with a fiber channel 1820 within, or adjacent to, which fiber bundle 1810 is secured—an objective lens 1920 transmits the excitation signal from excitation channel 1906 into each fiber 116 of fiber bundle 1810. Emissions from the emissions sources at the opposite ends of fibers 116 are transmitted by each fiber of fiber bundle 1810 back through objective lens 1920 and into optic channel 1904. Dichroic filter 1916 may be configured to reflect light of a specified emission wavelength. Thus, that portion of the emission light transmitted by fiber bundle 1810 into optics channel 1904 that is at the specified emission wavelength is reflected by the dichroic filter 1916 into the emission channel 1908.

An emission filter 1922 is disposed within the emission channel 1908 and is configured to transmit light having the desired emission wavelength. The emission channel 1908 terminates at a radial opening 1818 formed about the outer periphery of body 1806. In an embodiment, optics channel 1904 is oriented with respect to camera 1804 such that an optic channel 1904 that is in optical communication with fiber bundle 1810 is also in optical communication with camera 1804.

When optics channel 1904 is an operative position with respect to camera 1804, the radial opening 1818 of emission channel 1908 is aligned with image relay optics 1924 that transmit emission light from emission channel 1908 into camera 1804. Camera 1804 then images the emission signals transmitted by all fibers 116 in fiber bundle 1810 at once. To determine the signal transmitted by each fiber—and thus the signal emitted by the signal emission source associated with the fiber—the pixels of the camera's pixel matrix are mapped to the fiber locations within fiber bundle 1810 to identify the one or more pixels of the pixel array that correspond to each fiber 116. By interrogating the signal imaged at each pixel or group of pixels associated with a fiber, the signal (e.g. the color (wavelength) and/or intensity) of the emission signal transmitted by that fiber can be determined.

Suitable cameras include CMOS camera such as the IDS UI-5490HE camera or CCD camera such as the Lumenera LW11059 or the Allied GE4900. Preferably, the camera has at least 10 megapixels and has a high frame rate.

In an embodiment, the filter wheel 1802 includes multiple (e.g., 3 to 6) optics channels 1904, each configured to excite and detect an emission of a different wavelength or other specific, distinguishing characteristic. Thus by rotating filter wheel 1802 to index each optics channel 1904 with respect to fiber bundle 1810 and camera 1804, signals of each distinguishing characteristic can be measure from all fibers and associated signal emission sources.

It will be appreciated that the signal detector head may include one or more additional cameras positioned and be coupled to one or more additional fiber bundles to permit simultaneous imaging of the multiple fiber bundles.

Exemplary Optical Misalignment Diagnostic Methods

Exemplary methods of diagnosing an optical misalignment between (a) an optical component (e.g., channel, lens, filter, source, detector) of an optical signal detector head and an end of fiber 116 will now be described. Again, fiber 116 can be a multicore fiber having a plurality of cores 118 in which the relative spatial arrangement of cores 118 is preserved between the two ends of fiber 116. Such a multicore fiber 116 can be used to efficiently diagnose (i.e., determine the presence or absence of) an optical misalignment between various optical components of optical signal detector head and fiber 116. Any of the below described exemplary methods can be used with any frame assembly, including frame assemblies 102, 302, 802, and 1202 described herein, but for simplicity of the description, these methods will be described in the context of its implementation on frame assembly 102 shown in FIG. 1.

In some embodiments, an optical misalignment between (a) objective lens 1442 of signal detector 1308 or channel 1304 of base plate 1302 and (b) the end of fiber 116 coupled to base 112 can be diagnosed. Referencing FIGS. 14 and 15, the diagnostic method can include generating light using excitation source 1408 of signal detector 1308. The generated light passes through lens 1420 and filter 1422, reflects off mirror 1432, then reflects off dichroic filter 1434, exits objective lens 1442, and passes through channel 1304. The end of multicore fiber 116 (which is attached to base 112 of frame assembly 102) that is adjacent and optically coupled to channel 1304 and objective lens 1442 receives the light, and fiber 116 transmits the light to toward the end of fiber 116 attached to interface plate 106. This transmission generates an light pattern or image at the other end of fiber 116 attached to interface plate 106. This pattern can be generated either on fiber 116, itself, or on a signal coupling device 130 optically coupled to fiber 116.

Figure 20:
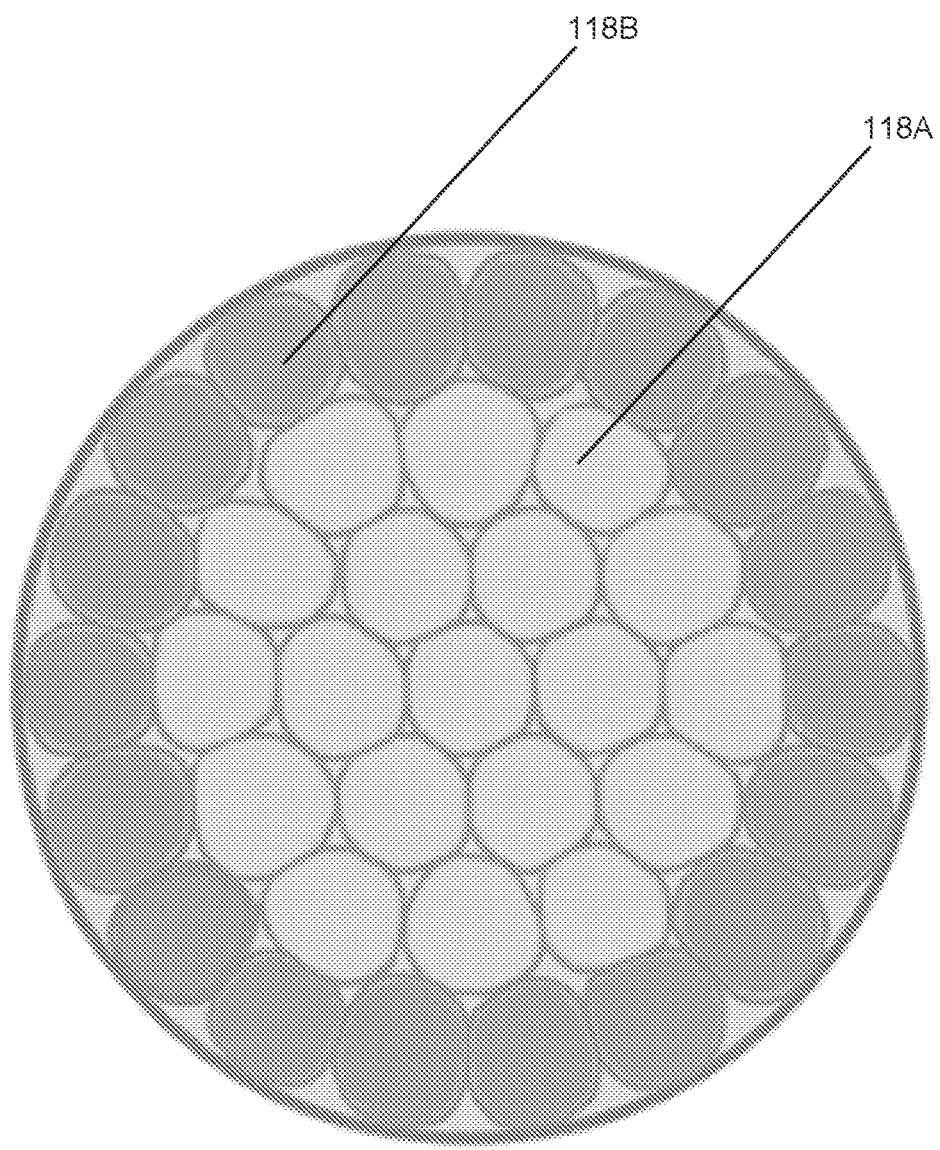
FIG. 20 is an image of a second end of the signal transmission fiber having a symmetric intensity pattern, according to an embodiment.

An optical misalignment between a component of signal detector 104 (e.g., objective lens 1442 of signal detector 1308 or channel 1304) and the end of fiber 116 coupled to base 102 and optically coupled to signal detector 104 can be diagnosed based on the symmetry (or asymmetry) of the resulting intensity pattern of the light pattern or image formed at the other end of multicore fiber 116. If the end of multicore fiber 116 (attached to base 112) adjacent and optically coupled to objective lens 1442 is optically aligned with objective lens 1442 and channel 1304, the resulting intensity pattern at the other end of multicore fiber 116 (formed directly on fiber 116, itself, or on signal coupling device 130) will be substantially symmetric. In the context of this application, symmetric means that the resulting pattern is symmetric about two perpendicular axes intersecting at the center of the pattern, and asymmetric means that the resulting pattern is not symmetric about one or both of such axes. FIG. 20 illustrates an exemplary symmetric intensity pattern of the end of multicore fiber 116. The cores 118A shaded with the light gray represent cores transmitting light with the greatest intensity. Cores 118A form a substantially circular, symmetric shape. The cores 118B shaded with a medium gray represent cores transmitting light with a slightly lower intensity than cores 118A at the center of the intensity pattern. These medium gray cores 118B form a substantially annular, symmetric shape. Collectively, cores 118A and cores 118B form a symmetric intensity pattern. This symmetric pattern shown in FIG. 20 is only exemplary, and other symmetric patterns may be formed. For example, the size, shape, and location of cores 118A and 118B may vary. And for example, there may be more than or less than two groups of cores with noticeably different intensities.

Figure 21:
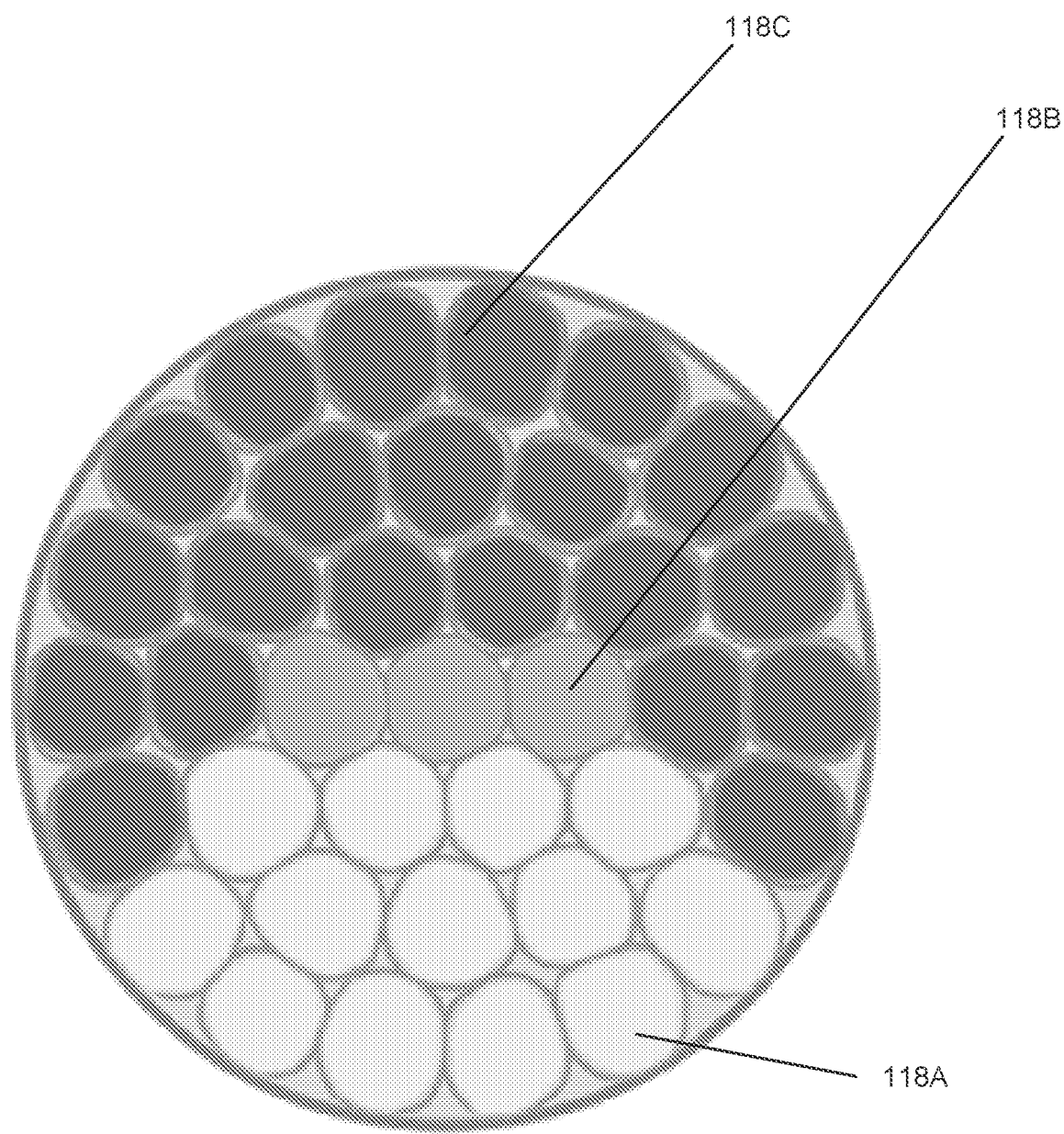
FIG. 21 is an image of a second end of the signal transmission fiber having an asymmetric intensity pattern, according to an embodiment.

If the end of multicore fiber 116 adjacent and optically coupled to objective lens 1442 is optically misaligned relative to objective lens 1442, the resulting intensity pattern at the other end of multicore fiber 116 will be asymmetric. FIG. 21 illustrates an exemplary asymmetric resulting intensity pattern at the other end of multicore fiber 116 (formed directly on fiber 116, itself, or on signal coupling device 130). The cores 118A shaded with light gray represent cores transmitting light with the greatest intensity. These cores 118A form a substantially trapezoidal shape at the bottom of the pattern. The cores 118B shaded with medium gray represent cores transmitting light with a lower intensity than cores 118A. These cores 118B form a substantially rectangular shape. The cores 118C shaded with dark gray represent cores transmitting light with a lower intensity than both cores 118A and 118B. These cores 118B form a substantially crescent-like shape at the top of the pattern. Collectively, the resulting intensity pattern formed by cores 118A, 118B, and 118C is asymmetric. This asymmetric pattern shown in FIG. 21 is only exemplary, and other asymmetric patterns may be formed. For example, the size, shape, and location of cores 118A, 118B, and 118C may vary. And for example, there may be more than or less than three groups of cores with noticeably different intensities.

Notably, the use of varying shades of gray in FIGS. 20 and 21 is for illustrative purposes only. In reality, the resulting color of cores 118 can be colors other than gray, for example, white, red, blue, green, orange, etc.

The symmetry or asymmetry of the resulting intensity pattern can be determined either manually or automatically.

In some manual embodiments, a person can visually inspect the image formed at the end of multicore fiber 116 (formed directly on fiber 116, itself, or on signal coupling device 130 at that end) to determine symmetry or asymmetry of the resulting intensity pattern. In some manual embodiments, this visually inspection can occur without the use of any other tools or devices. In other embodiments, this visually inspection includes using a magnifier to generate a magnified image of the end of the multicore fiber 116. Based on the visual inspection of the magnified image, the person can determine the symmetry or asymmetry of the resulting intensity pattern. The magnifier can be, for example, an electronic magnifying system having a camera system that acquires an image of the intensity pattern, and a display device that displays a magnified image of the acquired intensity pattern image. Or for example, the magnifier can be a magnifying glass.

In some automated embodiments, a camera system is used to automatically determine the symmetry or asymmetry of the resulting intensity pattern. The imaging device system can include, for example, a camera that acquires an image of the resulting intensity pattern at the end of multicore fiber 116. Suitable cameras include CMOS cameras and CCD cameras. The acquired image can then be processed to determine the symmetry or asymmetry of the resulting intensity pattern. For example, the pixels of the acquired image can be interrogated, either individually or in groups, to determine the symmetry or asymmetry of the resulting intensity pattern. In some embodiments, the camera system used for automatic determination is part of the sample assay instrument. In other embodiments, the camera system is a separate from the sample assay instrument.

Again, if asymmetry of the resulting intensity pattern is detected, the end of multicore fiber 116 adjacent and optically coupled to objective lens 1442 is optically misaligned relative to objective lens 1442 and channel 1304.

In some embodiments, the relative position of the end of multicore fiber 116 near and optically coupled to objective lens 1442 can be adjusted to reduce or eliminate the optical misalignment indicated by the asymmetric intensity pattern. The direction and magnitude of the relative position adjustment for correcting the optical misalignment can be determined based on the resulting asymmetric intensity pattern. That is, the resulting asymmetric intensity pattern can directly show the magnitude and direction of the misalignment because the relative spatial arrangement of cores 118 of fiber 116 is preserved between the two ends of fiber 116. For example, referencing FIG. 21, the location of the cores 118A having the greatest intensity at the bottom of the pattern indicates that the center of the optical element of the signal detector (e.g., the center of objective lens 1442 of signal detector 1308) is offset below (within the plane of the page as a reference) the detector-side end of fiber 116. Accordingly, if the signal detector is moved up (within the plane of the page as a reference) relative to the detector-side end of fiber 116 by about a half diameter of fiber 116, the optical misalignment will be reduced or eliminated. This reduction or elimination of misalignment after the positional adjustment can be confirmed by repeating the above steps and analyzing the symmetry or asymmetry of the resulting intensity pattern.

In some embodiments, signal detection head 104 and frame assembly 102 (to which fiber 116 is attached) are configured to allow for such relative position adjustment. For example, signal detection head 104 and frame assembly 102 can be configured to be securely coupled to each other at a plurality of different relative positions. In some embodiments, one of signal detection head 104 and frame assembly 102 defines an elongated channel that can receive a fastener or pin coupled to the other of the signal detection head 104 and frame assembly 102. Due to the elongation of the channel, the fastener or pin can slide within the channel to allow for the relative position adjustment between the end of multicore fiber 116 near (and frame assembly 102) and optically coupled objective lens 1442 of signal detection head 104. Once the desired relative position is achieved (i.e., when the end of multicore fiber 116 adjacent and optically coupled objective lens 1442 are optically aligned), the signal detection head 104 and frame assembly 102 can be securely coupled together in a fixed manner (e.g., by tightening a fastener that thereby prevents relative movement).

In some embodiments, the above described diagnostic method can be performed during the manufacturing stage of a sample assay instrument that uses the signal detector and optical fiber. That is, the method is performed before the sample assay instrument is received by the end-user. In other embodiments, the above described diagnostic method can be performed as part of a maintenance routine or while troubleshooting a problem at the customer site.

Hardware and Software

Aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as keyboards, touch screens, microphones, switches, manually-operated scanners, etc. Data output components may comprise hard drives or other storage media, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the disclosures require features or combinations of features other than those expressly recited in the claims. Accordingly, the present invention is deemed to include all modifications and variations encompassed within the spirit and scope of the following appended claims.

While various embodiments of the present invention have been described above, it should be understood that they have been presented by way of example, and not limitation. It will be apparent to persons skilled in the relevant art that various changes in form and detail can be made therein without departing from the spirit and scope of the invention.

The present invention has been described above with the aid of functional building blocks and method steps illustrating the performance of specified functions and relationships thereof. The boundaries of these functional building blocks and method steps have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof. Thus, the breadth and scope of the present invention should not be limited by any of the above-described exemplary embodiments, but should be defined only in accordance with the following claims and their equivalents.

Although specific embodiments are described above, as a person skilled in the art would recognize, many variations of the disclosed embodiments are possible, and therefore, within the scope of this disclosure.

What is claimed is:

1. An apparatus for detecting an optical signal emission from a plurality of signal emission sources, comprising:
    a plurality of signal transmission fibers each comprising a plurality of cores having a first spatial core arrangement at a first end and a second spatial core arrangement at a second end that is the same as the first spatial core arrangement, each first end being configured to be optically coupled to a respective signal emission source, and each fiber being configured to transmit an optical signal emitted between the first end and the second end;
    a frame assembly securing the first ends of the plurality of signal transmission fibers in a first spatial fiber arrangement corresponding to a spatial arrangement of the signal emission sources, and securing the second ends of the plurality of signal transmission fibers in a second spatial fiber arrangement different from the first spatial fiber arrangement;
    at least one signal detector configured to detect an optical signal emitted by each signal emission source; and
    a camera system configured to: (1) acquire an image of an intensity pattern of an optical signal emitted by the at least one signal detector and transmitted from the first end of at least one of the signal transmission fibers to a second end of the at least one of the signal transmission fibers, and (2) determine whether the acquired image of the intensity pattern of the transmitted optical signal is symmetric or asymmetric.

2. The apparatus of claim 1, wherein:
    the at least one signal detector comprises a plurality of signal detectors, wherein each signal detector is configured to generate an excitation light of a different predetermined wavelength and to detect light of a different predetermined emission wavelength; and
    the apparatus further comprises a signal detector carrier having mounted thereon the plurality of signal detectors, the signal detector carrier being configured to move such that each signal detector is sequentially and optically coupled to the second ends of the plurality of signal transmission fibers.

3. The apparatus of claim 1, wherein the first spatial fiber arrangement is rectangular and comprises two or more rows, each row including two or more of the first ends of the signal transmission fibers.

4. The apparatus of claim 1, wherein the second spatial fiber arrangement comprises one or more circles each comprising a plurality of second ends of the plurality of signal transmission fibers.

5. The apparatus of claim 4, wherein the signal detector carrier comprises a rotatable carousel configured to move the one or more signal detectors along a circular path corresponding to the one or more circles of the second spatial fiber arrangement.

6. The apparatus of claim 1, wherein the frame assembly comprises:
    an interface plate securing the first ends of the plurality of signal transmission fibers in the first spatial fiber arrangement; and
    a base, spaced apart from the interface plate, securing the second ends of the plurality of signal transmission fibers in the second spatial arrangement.

7. The apparatus of claim 1, further comprising a plurality of signal coupling elements, each being operatively optically coupled to a respective first end of each signal transmission fiber.

8. The apparatus of claim 1, wherein a minimum bend radius of the plurality of signal transmission fibers is equal to or less than about 10 mm.

9. The apparatus of claim 8, wherein the minimum bend radius of the plurality of signal transmission fibers is equal to or less than about 5 mm.

10. The apparatus of claim 1, wherein the plurality of cores comprises more than 15 cores.

11. The apparatus of claim 10, wherein the plurality of cores comprises at least 37 cores.

12. The apparatus of claim 1, wherein:
    each core of the plurality of cores comprises polymethyl methacrylate (PMMA); and
    each core of the plurality of cores is encased by a cladding comprising a fluorinated polymer.

13. The apparatus of claim 1, wherein each core has a non-circular cross-sectional shape.

14. A method of diagnosing an optical misalignment between a signal detector and a first end of a signal transmission fiber, the method comprising the steps of:
    emitting an optical signal from the signal detector;
    transmitting the emitted optical signal from the first end of the signal transmission fiber to a second end the signal transmission fiber;
    determining whether an intensity pattern of the transmitted optical signal is symmetric or asymmetric,
    wherein a symmetric intensity pattern indicates that the signal detector and the first end of signal transmission fiber are optically aligned, and
    wherein an asymmetric intensity pattern indicates that the signal detector and the first end of the signal transmission fiber are optically misaligned.

15. The method of claim 14, wherein the determining step is manual.

16. The method of claim 15, wherein the determining step comprises visually inspecting the intensity pattern.

17. The method of claim 16, wherein the visually inspecting step comprises using a magnifier that generates a magnified image of the intensity pattern.

18. The method of claim 17, wherein the magnifier comprises a magnifying glass.

19. The method of claim 17, wherein the magnifier comprise a camera system comprising a camera and a display that displays the magnified image.

20. The method of claim 14, wherein the determining step is automatic.

21. The method of claim 20, wherein the determining step comprises:
    acquiring an image of the intensity pattern; and
    automatically analyzing the acquired image to determine whether the intensity pattern of the transmitted optical signal is symmetric or asymmetric.

22. The method of claim 14, further comprising, when the intensity pattern of the transmitted optical signal is asymmetric, adjusting the relative position between the signal detector and the first end of the signal transmission fiber.

23. The method of claim 22, wherein at least one of a magnitude and a direction of a relative position adjustment between the signal detector and the first end of the signal transmission fiber is determined based on the intensity pattern.

24. The method of claim 14, wherein the emitting, transmitting, and determining steps occur during the manufacturing process of a sample assay instrument comprising the signal detector and the signal transmission fiber.

25. The method of claim 14, wherein the emitting, transmitting, and determining steps occur during routine maintenance of a sample assay instrument comprising the signal detector and the signal transmission fiber, or while trouble shooting a problem with the diagnostic instrument after manufacturing.

* * * * *

UNITED STATES PATENT AND TRADEMARK OFFICE
CERTIFICATE OF CORRECTION

PATENT NO. : 11,585,760 B2
APPLICATION NO. : 16/633985
DATED : February 21, 2023
INVENTOR(S) : Norbert Hagen, George Walker, II and David Combs It is certified that error appears in the above-identified patent and that said Letters Patent is hereby corrected as shown below:

On the Title Page

In Item (57), under "ABSTRACT", in Column 2, Line 6, delete "second." and insert --second end. --, therefor.

In the Specification

In Column 1, Line 52, delete "second." and insert -- second end. --, therefor.

In Column 2, Line 40, delete "end the" and insert -- end of the --, therefor.

In Column 3, Line 19, delete "operational" and insert -- operation --, therefor.

In Column 5, Line 10, delete "capable performing" and insert -- capable of performing --, therefor.

In Column 5, Line 17, delete "capable performing" and insert -- capable of performing --, therefor.

In Column 5, Line 51, delete "reactions (TMA)," and insert -- (TMA) reactions, --, therefor.

In Column 5, Line 52, delete "reactions (SDA)," and insert -- (SDA) reactions, --, therefor.

In Column 8, Line 8, delete "used a" and insert -- used in a --, therefor.

In Column 8, Line 19, delete "synthesis" and insert -- synthesis at --, therefor.

In Column 8, Line 47, delete "an frame" and insert -- a frame --, therefor.

In Column 9, Line 22, delete "2500µ." and insert -- 2500µm. --, therefor.

Signed and Sealed this
Eighth Day of August, 2023

Katherine Kelly Vidal
*Director of the United States Patent and Trademark Office*

CERTIFICATE OF CORRECTION (continued)
U.S. Pat. No. 11,585,760 B2

In Column 11, Line 38, delete "polyethylene ketone (PEEK)." and insert -- polyether ether ketone (PEEK). --, therefor.

In Column 12, Line 5, delete "based one" and insert -- based on one --, therefor.

In Column 20, Line 18, delete "anneal" and insert -- be to anneal --, therefor.

In Column 20, Line 19, delete "second" and insert -- seconds --, therefor.

In Column 22, Line 19, delete "excitations" and insert -- excitation --, therefor.

In Column 22, Line 55, delete "is an" and insert -- is in an --, therefor.

In Column 23, Line 14, delete "measure" and insert -- measured --, therefor.

In Column 24, Line 56, delete "visually" and insert -- visual --, therefor.

In Column 24, Line 58, delete "visually" and insert -- visual --, therefor.

In Column 25, Lines 14-15, delete "is a separate" and insert -- is separated --, therefor.

In the Claims

In Column 28, Line 34, in Claim 14, delete "end the" and insert -- end of the --, therefor.